United States Patent
Kelly, Jr. et al.

(10) Patent No.: US 7,127,370 B2
(45) Date of Patent: Oct. 24, 2006

(54) ATTITUDE INDICATOR AND ACTIVITY MONITORING DEVICE

(75) Inventors: Paul B. Kelly, Jr., Fair Oaks, CA (US); Donald W. Schoendorfer, Santa Ana, CA (US); Jeffrey L. Simmons, Lake Forest, CA (US)

(73) Assignee: NOCWatch International Inc., Crystal Bay, NV (US)

( * ) Notice: Subject to any disclaimer, the term of this patent is extended or adjusted under 35 U.S.C. 154(b) by 0 days.

(21) Appl. No.: 10/411,631

(22) Filed: Apr. 11, 2003

(65) Prior Publication Data

US 2004/0010390 A1 Jan. 15, 2004

Related U.S. Application Data

(63) Continuation of application No. 09/755,840, filed on Jan. 5, 2001, now Pat. No. 6,611,783, which is a continuation-in-part of application No. 09/479,558, filed on Jan. 7, 2000.

(51) Int. Cl.
 *G01C 9/06* (2006.01)
 *G08B 21/00* (2006.01)
 *H01H 35/02* (2006.01)

(52) U.S. Cl. .................... 702/151; 340/573.1

(58) Field of Classification Search ........ 702/150–151, 702/141, 154; 340/573.1, 539.12, 689, 587; 600/587

See application file for complete search history.

(56) References Cited

U.S. PATENT DOCUMENTS

| | | | | | |
|---|---|---|---|---|---|
| 4,232,308 | A | * | 11/1980 | Lee et al. | 340/539.3 |
| 5,263,491 | A | * | 11/1993 | Thornton | 600/587 |
| 5,398,019 | A | * | 3/1995 | Barnett et al. | 340/573.7 |
| 5,751,214 | A | * | 5/1998 | Cowley et al. | 340/573.4 |
| 5,982,285 | A | * | 11/1999 | Bueche et al. | 340/573.1 |
| 6,160,478 | A | * | 12/2000 | Jacobsen et al. | 340/539.12 |
| 6,201,476 | B1 | * | 3/2001 | Depeursinge et al. | 340/573.1 |
| 6,285,899 | B1 | * | 9/2001 | Ghaem et al. | 600/391 |
| 6,301,964 | B1 | * | 10/2001 | Fyfe et al. | 73/510 |
| 6,307,481 | B1 | * | 10/2001 | Lehrman et al. | 340/669 |
| 6,547,745 | B1 | * | 4/2003 | Rubinstein | 600/549 |

* cited by examiner

Primary Examiner—Marc S. Hoff
Assistant Examiner—Manuel L Barbee
(74) Attorney, Agent, or Firm—Lee & Hayes, PLLC

(57) ABSTRACT

An attitude indicator device for detecting, indicating, and/or logging the positional attitude of an individual in response to deviation from a set of one or more reference angles. By way of example and not of limitation, the device is mounted on the thigh of a patient and measurements are taken from an acceleration sensor within the device. The acceleration measurements are communicated to a receiver when the measurements deviate from acceptable thresholds, whereby the receiver indicates an alert condition. The device may be employed within numerous medical related applications, for example, to facilitate preventing patient egress and the prevention/detection of patient falls.

16 Claims, 10 Drawing Sheets

ATTITUDE INDICATOR AND ACTIVITY MONITORING DEVICE

PRIORITY DATA

This application is a continuation of application Ser. No. 09/755,840, filed Jan. 5, 2001, now U.S. Pat. No. 6,611,783 which is a continuation-in-part of application Ser. No. 09/479,558 filed on Jan. 7, 2000, both incorporated herein by reference.

BACKGROUND (1) Field of the Invention

This invention pertains generally to medical devices for patient monitoring, and more particularly to a system for monitoring the orientation of an individual wherein remote indications of said orientation are generated.

(2) Prior Art

Injuries sustained from falls, such as by the elderly and patients within a medical facility, can be both debilitating and costly. The social and economic costs associated with falls in the elderly have been described as "staggering" and a "public health problem of crisis proportions" (Hayes 1996). It is also a growing problem within the population as the fastest-growing segment of society are those over 65 years of age. Trends indicate that the nation's senior citizens are becoming increasingly frail, functionally dependent, and more ill than their recent counterparts (Evans 1995).

One out of every three individuals over age 65, and half of those over age 80, experience a fall each year; this percentage equates to about 10 million US residents. Falls are the leading cause of injury deaths and disabilities in this age group (Kiely 1998, NINR 1994, Rubenstein 1994). Falls account for 87% of all fractures within individuals over age 65 and are the second leading cause of spinal cord and brain injury among older adults (CDC 2000b).

Hip fractures are a common injury sustained by the elderly during such falls. The current 34 million in this population group will double in the next 40 years, and it is clear that without effective intervention strategies, the number of hip fractures will increase as the U.S. population ages (CDC 2000c). Per statistics from the Center for Disease control and Prevention, the estimated $20 billion (1994) in US direct health care costs each year due to falls continues to rise at a rate faster than the elderly population is growing. A successful reduction in fall rate would thus predict significant potential for commercial success.

The situation is especially egregious for the most frail and ill of our elderly, currently about two million of us, that require full-time care in a skilled nursing facility. Within skilled nursing facilities the residents take an average of 7.2 medications (Evans 1995), and two out of three fall at least once each year (Cooper 1997, Evans 1995). The majority of falls among the elderly within skilled nursing facilities occur in their own rooms as they attempt to get up out of the bed, without assistance, to use the lavatory at night (Alcee 2000, Capezuti 2000, Evans 1998).

In addition, numerous cases of falls occur among those with mental disorders. As many as 90% of the residents of skilled nursing facilities suffer from some form of mental disorder, including dementia (Evans 1995). An individual suffering from any form of mental confusion, whether endemic or due to the effect of medication, is subject to an increased risk of falling due to the associated impairment of judgment, lack of visual-spatial perception, loss of ability to orient themselves geographically (Rubenstein 1994), inability to understand, or impaired memory functions (Evans 1998).

In the past, patients considered to be at a high risk of falling were often restrained to their beds to prevent unassisted egress; however, it will certainly be appreciated that such treatment is contrary to the dignity of the patient. Furthermore, the use of restraints is generally impractical and it is often illegal (Health Care Reform Act of 1994). Another drawback is the inherent difficulty in attempting to accurately identify individuals that have a high likelihood of falling.

A variety of protective garments and protection devices have been studied for reducing fall-induced injuries, in particular hip fractures. In one such device, protective pads are retained proximal to the greater trochanter (upper portion of the hip bone), within a garment to displace the impact forces of a fall. Wearing these protective garments has been shown to provide a measure of protection against hip fractures, however, a large percentage of patients either refuse to wear the protective garments or become non-compliant with regard to use over time.

Recently, individuals have been monitored utilizing devices in which the individual or patient is harnessed to the monitoring device by means of wiring. These devices can be cumbersome and often restrain the movements of an individual. The benefits derived from monitoring the position and/or movement of an individual or patient have long been appreciated, and a number of monitoring devices have been considered.

The effectiveness of current devices for monitoring position or activity has been limited for several well-known reasons. Often such devices are unreliable as they rely on pendulums, mercury switches, or other forms of mechanisms that do not provide reliable detection. The majority of these devices are prone to the generation of false positives due to these inherently unreliable sensing mechanisms. Ultimately, as a result of the false alarms, the wearer or caregiver becomes conditioned to ignore the alarm, thereby negating any possible benefits that may have otherwise been derived. Unreliable sensing is particularly troublesome for devices that are not directly worn by the subject, such as pressure-activated devices, that indirectly infer subject orientation or activity.

As a group, the devices can be difficult to operate, or their operation may be suitable only for limited clinical use. A level of cognitive functioning and mental alertness is often required of those wearing the devices. This limitation can preclude the use of these devices for a substantial percentage of potential users who may be confused, disoriented, or unconscious and thus unable to activate the device.

Devices that are worn directly by a subject tend to be large, bulky, awkward, and/or uncomfortable which limits user acceptance and concomitant use. Several devices are further limited with regard to their applicability, as they may need to be worn by the human subject in a way that restrains the individual and/or comprises human dignity. Limited mobility is one particularly strong objection to many such devices which require the subject to be "attached" to the device by way of restrictive harnesses, belts, tethers, cords, cuffs, bracelets, elastic bands, or the like.

Devices requiring the aforementioned attachments are not suitable for continuous wear by an individual, and periodic disconnection is required to accommodate a number of activities, such as bathing. The restriction of movement caused by these devices is obtrusive and can noticeably interfere with sleep or daily activities. Not surprisingly, the interference that need be endured when using these devices compromises their acceptance and effectiveness. The relatively high cost of these devices is often further exacerbated by their associated methods of use which subject the devices to both damage, such as from inadvertent washing, and from theft. A further complication often arises after one of these devices becomes damaged or otherwise needs to be disposed of, because the commonly used mercury switches within the devices present a special waste disposal requirement that can be particularly challenging within a health care facility.

Attempts to solve the foregoing problems employing an assortment of electro-mechanical alarms have been largely met with failure. The actual liability associated with falls is so high that we see increasing use of these devices, apparently just to make patients and their families feel like "something" is being done, even though they are costly and ineffective. One of these problematic devices attempts to monitor the bed, or floor area near the bed, for changes in applied force. The device was found to generate false positives while being difficult to maintain and cumbersome. Independent reviews of additional devices currently on the market have concluded that no device exists which has been successful at reducing the rate of falls, and that a portion of these device types were actually associated with an increase in the incidence of falls.

The drawbacks associated with the current monitoring devices are regrettable in view of the serious nature and sheer number of injuries which are sustained from falls. Applicable subjects for attitude monitoring include a wide range of patients, and in particular those recovering from surgery or stroke, those under the influence of medications, elderly individuals in a weakened condition or suffering from dementia, or normally active individuals whose temporary condition has placed them at risk of falling. It will be appreciated that subject movement may be involuntary, such as in the case of sleepwalking, and that serious injuries may result from such movement due to a fall or the dislodgment of medical devices, which may include fluid supplies, air supplies, drainage connections, or monitoring devices. One commonly cited condition of those experiencing a fall is an altered mental state; therefore, it will be appreciated that if a device is to be successful it should not require cognitive functioning on the part of the user for activation.

Monitoring the physical activity of a subject can provide benefits within a number of applications. These include patient safety, activity studies on humans, studies on laboratory animals, compliance programs for postoperative rehabilitation or physical therapy, ensuring proper posture or sleeping position, preventing patients from becoming ambulatory without assistance, detecting subject loss of consciousness, controlling post surgical movement, or determining whether set levels of activity are being achieved.

Therefore, a need exists for a non-cumbersome device that is capable of providing reliable monitoring of subjects without the aforementioned drawbacks that are inherent in current devices. The present invention satisfies those needs, as well as others, and overcomes the deficiencies of previously developed attitude indicators and monitoring devices.

SUMMARY OF THE INVENTION

The present invention provides a device and method of monitoring the orientation of an individual with a miniature attitude-sensing unit capable of communicating orientation alerts for registration on a receiver unit. Registration comprises reception followed by identification, attitude recognition, or activity characterization, along with displaying, annunciating, or logging the transmitted conditions. The attitude-sensing unit comprises an orientation sensor and signal transmitter that are attached to the individual being monitored, preferably on the thigh of the individual. It should be appreciated that although the subject is typically human, the subject may alternatively comprise an animal under medical care or study, or an object in association with a human, or animal, possibly under medical care or study. The attitude indicator and activity-monitoring device of the present invention may additionally be referred to herein as an "attitude indicating device", or simply "device", and it generally comprises an attitude transmitter unit coupled with a receiver unit.

By way of example and not of limitation, one embodiment of the present invention provides for monitoring the orientation of a human subject based on the orientation of a specific portion of the subject's body upon which the attitude transmitter unit has been positioned. One aspect of the invention is the transmission of alert signals based on a comparison between the orientation of the attitude transmitter unit, which is attached to the body of the subject individual, and a predetermined set of orientation criteria. If the orientation criteria are met, an alert is generated from the attitude transmitter unit to a receiver unit capable of indicating the alert condition. For example, the detection of rapid declination may be indicative of a fall.

A preferred application of the attitude indicating device is that of detecting intended egress by an individual. To detect patient egress, such as from a bed or wheelchair, an attitude transmitter unit is integrated within an appliance that is preferably attached to the posterior thigh, of the individual being monitored. An attitude receiver unit is located within range of the attitude transmitter unit to receive alert conditions and generate an indication of the alert in a form that may include, audio, visual, or tactile information. By way of example, the transmitter generates radio-frequency alert transmissions in response to changes in transmitter attitude that are characteristic of specific conditions. The alert transmissions are received by a receiver unit that generates audio alerts to attendants, or other nearby personnel.

The receiver unit may be configured to provide attitude, or activity, indication in a variety of forms, such as audible tones and/or words, discrete visual indicators, such as LEDs, various displays such as an alphanumeric LCD, or by remotely conveying attitude, or activity, information to another system. An example of conveying the information to a remote system may involve interfacing the attitude indication signals with an institutional monitoring system, such as a nurse's station capable of displaying the attitude information as status information, of generating audible alerts, of dispatching personnel, of generating a page, and so forth. It will be appreciated that the receiver unit may comprise more than one device; for example, a receiver positioned at a first location and operably connected to circuitry at a second location that performs the processing of the received signals. The circuitry at the second location may in turn be operably connected to another unit, and so forth. Any combination or level of integration can be supported insofar as one or more of the units, or devices, is capable of generating alerting signals that are responsive to the transmitter unit.

The attitude, and activity, indicating device of the present invention allows physical orientation to be indicated as a set of measurements, or by way of orientation alerts generated in response to attitude threshold conditions. Attitude and activity are preferably detected within the transmitter by utilizing an acceleration sensor that is capable of detecting attitude (tilt), and positional rate of change. An attitude transmitter configured to provide attitude measurements may transmit measured orientation information either in response to status changes or on a periodic basis. Alerting signals may be generated upon the measured conditions meeting one or more alert validation criteria. The receiver unit is capable of responding to the transmitted signals in a manner consistent with the application. For example, the receiver may generate an audio output in response to the alert signal, or it may record, display, communicate, and/or analyze the attitude or acceleration data contained within a transmission.

In a basic application of the attitude indication device, the attitude transmitter unit generates an alert signal when the thigh of the patient changes from a generally horizontal plane, as would exist for a patient lying in bed, to a specific downward angle characteristic of the patient getting out of bed in preparation for walking. The attitude transmitter unit may additionally be configured for generating periodic signals, such as measurements, or an "alive" signal. In the absence of measurements, or status changes, being transmitted to the remote unit, an alive signal may be periodically transmitted to provide an indication to the remote attitude receiver unit that the attitude transmitter is still "alive", insofar as it is operating properly and remains within reception range. When configured to receive a periodic alive signal, the attitude receiver unit is capable of generating an alert to personnel if the transmitter unit has left the vicinity (reception range) of the receiver, or has experienced a malfunction. It should be appreciated that alive signal generation is preferably combined with the use of alert signal generation, so that alerts may be detected in response to events while the conveyance of periodic status information is accommodated to provide notification of undesired patient ambulation or system failures.

The attitude indicator device of the present invention may be utilized within a variety of diverse medical applications, which include but are not limited to: preventing/detecting patient egress, preventing/detecting patient falls, monitoring infants, detecting the onset of labor in horses, tracking physiological activity of patients, use in physical therapy, detecting range of motion, monitoring epileptics for seizures, limiting post surgical patient movement, limiting the motion of unconscious patients recovering from surgery, monitoring for sleep apnea and snoring, alerting employers of unsafe worker activity, detecting improper standing sleeping or lifting posture, and detecting lapses of consciousness.

The attitude receiver unit can be adapted to provide alerts and attitude monitoring to suit a variety of environments, which for instance may include: in-room alarms, remote alarms, wearable alarms, and institutional alarms. The attitude receiver unit may be configured to generate an indication to personnel that comprises one or more forms of output generated from a visual, audible, or tactile feedback source. The feedback alerts the wearer and/or supervisory personnel of subject conditions for which an action may be indicated, examples of which are subject egress or attempted ambulation. The output of an attitude receiver unit configured to receive attitude measurement information may additionally be connected to a data-logging unit to provide for future analysis. Furthermore, the attitude receiver unit may be integrated into various standard communication systems, such as those connected to the Internet, as well as pagers, cellular phones and various wireless communication protocols, such as those based on the Bluetooth standard. The receivers may also be integrated into custom or institutional communication systems, such as systems associated with a nurse's station or other systems designed to support the alerting of personnel.

The attitude transmitter unit of the present invention comprises an orientation sensor coupled to a radio-frequency (RF) transmitter. The orientation sensor is preferably implemented as an acceleration sensor, although alternative means for sensing positional attitude in up to three dimensions may be utilized. In an aspect of the invention, the threshold conditions under which an alert signal is to be generated by the attitude transmitter unit may be set according to the particular application being addressed. The attitude transmitter unit embodied herein is small, lightweight, wireless, waterproof, shockproof, unobtrusive to the wearer, may be worn continuously for several consecutive days, and does not require that the wearer be cognitively functional. It can be adhered to various body parts according to the requirements of the medical application being addressed, or incorporated into clothing, headgear, bandages, inanimate objects, and so forth. Communication between the attitude transmitter unit and an attitude receiver unit is preferably by way of a radio frequency link; however, alternate forms of communication may be employed, comprising forms such as inductive coupling, infrared, ultraviolet, audio, and ultrasonic.

The present design further anticipates an embodiment of the attitude transmitter that utilizes a transponder mechanism, such as an RF transponder, wherein the receiver (or other external device) is configured to generate a first transmission to which the transmitter responds with a responsive second transmission. The power for the transmitter and attitude sensing circuits are thereby derived from the received power of the first signal, wherein no batteries need to be provided within the transmitter. The available transmitter operating power derived from a transponder circuit is, however, limited in that an alternative acceleration sensor having a lower power dissipation is necessary to provide reliable operation.

The attitude receiver unit may be configured so that the individual wearing the attitude transmitter unit is alerted to the attitude conditions, wherein the device provides real-time feedback that is capable of training a wearer to maintain a desired position, or range of positional attitudes. Patient feedback can be especially useful with postoperative patients directed to limit certain forms of movement during the recovery process. The attitude transmitter unit is also configured for detecting its own removal from the body of the individual to which it is attached, whereupon it preferably generates an alert signal so that the associated attitude receiver unit can generate an indication, such as an audible alarm.

Attitude indication devices can be configured for a stand-alone system wherein a single transmitter is associated with a single receiver in combination, or may alternatively be integrated into a custom or existing receiver/annunciation system and configured to receive data from any number of attitude transmitter units. The attitude transmitter unit may be manufactured in an array of shapes and sizes in accord with specific applications, while the preferred solid-state design anticipates further miniaturization to facilitate both unobtrusive attachment and/or implantation. In addition, when an attitude transmitter unit is no longer necessary, or serviceable, it may be either recycled or disposed of without environmental impact considerations (such as the special handling requirements of mercury switch-containing devices).

Subject attitude is preferably determined within the attitude transmitter unit by way of a solid-state orientation sensor capable of providing orientation information in relation to the portion of the individual's body to which it is attached. It will be appreciated that integrated circuit sensors, such as acceleration sensors, are generally still considered to be "solid-state" devices although they often incorporate micro-electromechanical systems (MEMs). A solid-state orientation sensor that registers orientation measurements is preferred over the use of a mechanical switch that is generally limited to a non-linear on/off mode of response. The output of a mechanical switch is not generally well suited for medical attitude/activity monitoring due to the large proportion of false alarms generated and the difficulty involved with qualifying a discrete event that is subject to mechanical vibration, inertia, and electrical noise.

A preferred solid-state orientation sensor comprises an acceleration sensor configured to register acceleration in at least one plane of motion. When retained in a static orientation, the acceleration sensor provides orientation data in response to the force of earth's gravitation, the resulting static force being up to one gravitation (G) unit on any of the three axes. In contrast to a tilt sensor, the acceleration sensor additionally provides rate of change information that may be utilized to further qualify prospective events. Therefore, it will be appreciated that the data provided by the acceleration sensor within the attitude transmitter unit can be used to enhance the accuracy of attitude or activity information, whether detecting patient falls, attempted egress, slips, transmitter removal, seizures, as well as other situations that may be characterized in relation to positional attitude and changes thereto.

An object of the invention is to provide a device capable of indicating and monitoring the physical attitude of an individual.

Another object of the invention is to provide a reliable solid-state device for sensing positional attitude in up to three dimensions.

Another object of the invention is to provide a reliable wireless device for monitoring the positional attitude of an individual.

Another object of the invention is to detect patient egress and to communicate an associated alert to mitigate the risk of falls.

Another object of the invention is to provide selection of the angle of displacement for which the device will produce a desired alert signal.

Another object of the invention is to provide a device and method of sensing subject attitude as may be applied to human, non-human, and inanimate subjects (objects).

Another object of the invention is to provide a device that may be reused or disposed of without special environmental or waste handling requirements.

Another object of the invention is to provide a monitoring device that is small, lightweight, and unobtrusive.

Another object of the invention is to provide a robust monitoring device that is not easily damaged or broken, and whose method of use reduces the probability of detachment, loss or theft.

Another object of the invention is to provide a device that is waterproof and shockproof.

Another object of the invention is to provide a low-cost device which may be readily disposed of when no longer needed, or serviceable.

Another object of the invention is to provide a monitor that is compatible with the activities of a human subject, such that it may be worn for several consecutive days without the need of restricting the subject from bathing, showering, and so forth.

Another object of the invention is to provide a monitoring device whose use does not require the wearer to be cognitively functional.

Another object of the invention is to provide a monitor that may be worn on various body parts according to the needs of the user, or incorporated into such items as medical appliances, rehabilitation appliances, trusses, clothing, shoes, or headgear.

Another object of the invention is to provide an attitude monitoring system that provides a wireless connection between an attitude detector and a remote attitude indication unit so that wearers need not be "tethered" by an electrical cord to an electrical device.

Another object of the invention is to create a device capable of providing real-time feedback so that a wearer may be conditioned to maintain a desired positional attitude, or range of motion, without the necessity of constant supervision.

Another object of the invention is to provide a monitoring device that is compatible with both stand-alone systems, wherein one transmitter is associated with one receiver, and integrated (institutional) systems wherein signals from multiple transmitters are detected by one or more receivers.

Another object of the invention is to provide a monitoring device capable of transmitting a signal, or data, to either stationary or portable receiver systems (nearby or remote), depending on the needs of the user.

Another object of the invention is to provide a device that may be manufactured in various sizes in accordance with the intended application, and in particular which may be miniaturized for implantation purposes.

Another object of the invention is to provide an attitude monitoring device which is capable of measuring both static and dynamic acceleration to properly distinguish events, for example, it is able to distinguish between an individual changing sleeping positions and attempted egress.

Another object of the invention is to provide an attitude transmitter unit configured to detect when it is being removed from a subject, whereupon it responds by generating an alerting signal.

Another object of the invention is to provide a monitoring device that can be readily manufactured at low cost.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings that are for illustrative purposes only.

DETAILED DESCRIPTION OF THE INVENTION

Referring more specifically to the drawings, for illustrative purposes the present invention is embodied in the apparatus generally shown in FIG. 1 through FIG. 10. It will be appreciated that the apparatus may vary as to configuration and as to details of the parts, and that the method may vary as to the specific steps and sequence, without departing from the basic concepts as disclosed herein.

Figure 1:
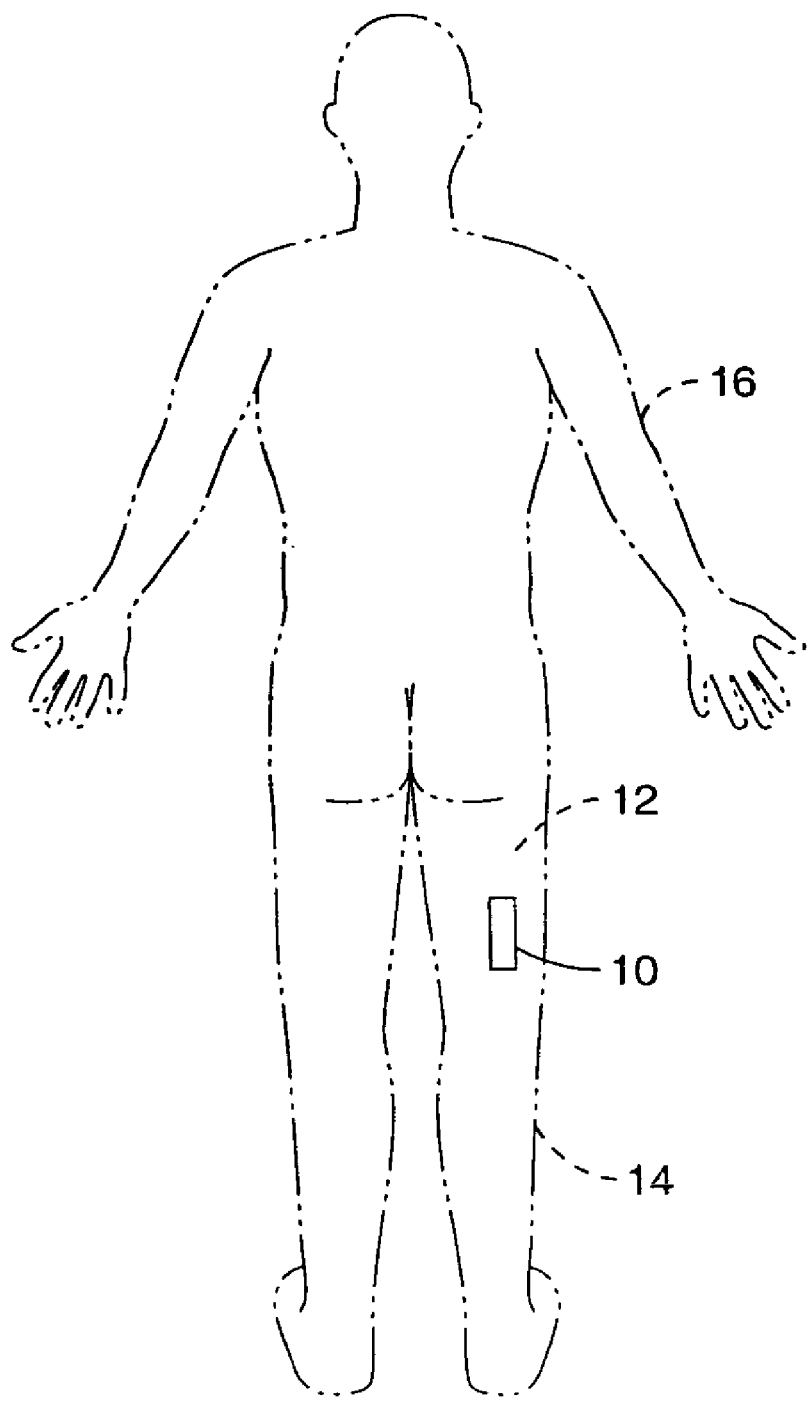
FIG. 1 is a diagram of an attitude transmitter unit according to the present invention shown in a preferable operating position attached to the posterior thigh of an individual.

Referring first to FIG. 1, the attitude indication device 10 of the present invention is shown, by way of example, being worn on the posterior thigh region 12 on the leg 14 of an individual 16 (shown in phantom). The preferred apparatus comprises an orientation sensor within an attitude transmitter unit that is worn as a medical appliance, or patch, on the individual's thigh and that is operatively coupled for communication with a remote attitude-receiving unit. The attitude transmitter unit may be attached to the individual's body at any location consistent with its intended application, however, it has been determined that by properly configuring the attitude indicator and mounting it on the thigh, an example of which is shown in FIG. 1, patient egress may be detected prior to ambulation while false alarms may be minimized.

In arriving at the preferred embodiment of the invention, a significant volume of data relating to falls in addition to associated injury statistics were compiled and analyzed for patterns from which a remediation strategy could be developed. From analyzing the data, it became apparent that a substantial percentage of falls are the result of individuals under supervised care attempting unsupervised self-ambulation, such as within a hospital, nursing home, or similar institutional setting. Proper remediation, therefore, would require the ability to reliably anticipate and detect attempted egress in specific situations.

A variety of proposed and current devices were considered in the subject application, and found to be lacking in one or more significant areas. In attempting to find a reliable, inexpensive, and easy-to-implement detection method, a number of anatomical models were studied with regard to both device placement and characterization of movement. After numerous alternative detection mechanisms were considered, it was found that the position of the long axis of the femur may be the most definitive indicator of the position of an individual in relation to the detection of egress. Prior to attempting self-ambulation, it will be appreciated that an individual must first stand, wherein the femur will be inclined to a downward angle of at least seventy degrees from the horizontal. If the angle of the femur is constrained to shallow downward angles for the supine or sitting patient, no standing egress would be possible from a bed, or chair. Therefore, the conditions under which the femur, or associated thigh, of a supine or sitting patient can be declined at a sufficient downward angle are highly indicative of egress, and or attempted ambulation.

The posterior region of the thigh generally follows the movement of the long axis of the femur and is the preferred location for positioning the attitude detector on the individual within the present invention. In addition, the middle to lower posterior thigh is one of the least sensitive portions of the body and is out of sight while providing only limited patient access. However, the transmitter unit may be alternately positioned on the thigh according to the needs and comfort of the patient.

Figure 2A:
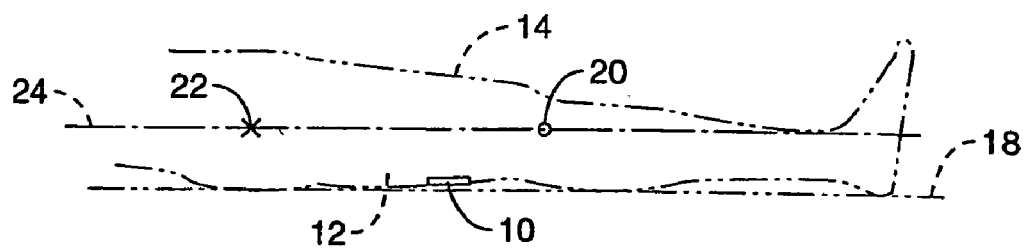
FIG. 2A is a diagram of the attitude-monitoring device according to the present invention adhesively attached to the thigh of an individual shown lying in a generally horizontal position.
Figure 2B:
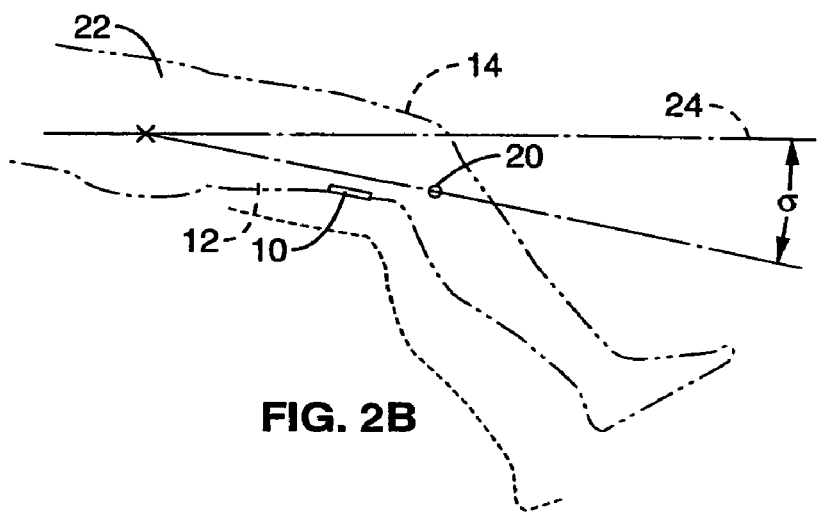
FIG. 2B is a diagram of the attitude indicator device of FIG. 2A shown angled as the leg of the individual moves downwardly.

Referring to FIG. 2A, while an individual is lying on a flat surface 18, such as a bed, it is difficult for thigh 12 to be inclined downwardly so that a knee 20 of the individual is retained at a significantly lower height than hip 22. The leg 14 of the individual shown in FIG. 2A is considered to be in a horizontal plane 24 as a line subtending the center of knee joint 20 (represented by an "o") and hip joint 22 (represented by an x) and is substantially on a horizontal plane. It will be appreciated, however, that in order for an individual to ambulate, they must first bring their legs 14 over the side of the bed in preparation for standing. Typically, the individual's thigh 12, as in FIG. 2B, traverses downwardly prior to the individual placing his or her feet on the ground as weight is increasingly transferred to the hip and knee joints, regardless of whether the individual is originally positioned on his or her back, chest or side. Similarly, for an individual to leave a chair, the thigh must likewise achieve a downward orientation in preparation for standing.

In summary, the act of standing or ambulating from a supine or sitting position is achieved by:
1. transferring body weight to hip and knee joints;
2. rotating and orienting the femur, of one or both thighs, to a vertical position;
3. transferring body weight through the femur and knee joint to one or both feet;
4. assuming a standing, or ambulating, position.

It will be appreciated that ambulation is difficult without the femur being retained in a mechanically advantaged vertical position.

Figure 3:
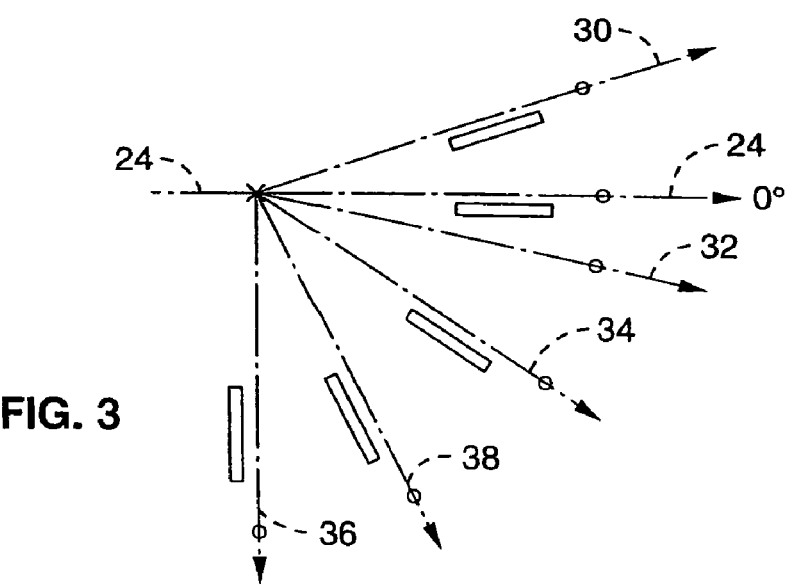
FIG. 3 is a schematic of angular device positions according to aspects of the present invention showing preferred and significant angular positions.

Referring now to FIG. 3, the orientation sensor within the attitude transmitter unit is responsive to the downward angle of the thigh, and according to one embodiment of the invention, the attitude indication device generates a signal if the thigh of the individual is oriented downwardly at an angle that indicates that the individual is in an undesired orientation. To prevent false triggering, the attitude indication device is configured to prevent the generation of alert signals in response to any angle above the horizontal as exemplified by angle 30. As the thigh is inclined downwardly, the angle at which the thigh must be oriented in order for a signal to be generated by the attitude detector varies depending on how the attitude transmitter unit has been configured for the applicable circumstances.

For example, when the attitude transmitter unit is attached to a comatose individual that is unlikely to move, it may be desirable to generate an alert signal for even slightly downward displacements of thigh 12 from horizontal plane 24. Thus, for such comatose individuals, the orientation sensor may generate a signal if the individual's thigh is at a slight downward angle 32 that preferably exceeds about five to fifteen degrees from horizontal plane 24. Preferably, the attitude transmitter unit is configured to ignore all upward angular displacements of the thigh, such as frequently may occur when an individual props up a knee, or elevates one leg.

When attached to generally mobile individuals, who are far more likely to shift position while lying on a bed, attitude indicator 10 may be configured to generate a signal when the individual's thigh exceeds a moderate downward angle 34 with respect to horizontal plane 24. The attitude indicator can be configured to generate an alert when the thigh of the individual exceeds an angle which may be adjusted within a range of downward angles between the slight downward angle 32 and a fully vertical angle 36. Those skilled in the art will appreciate that the angle at which the orientation sensor generates a signal may be any angle compatible with the intended use of the apparatus and the mobility of the individual.

During testing of the attitude indication device it has been determined that a downward threshold angle 38 of about seventy degrees is highly preferred as a detection threshold. This highly preferred detection threshold can range from between sixty degrees up to eighty degrees. By triggering the alert at a downward angle of the thigh that exceeds about seventy degrees, the occurrence rate of false alarms is significantly reduced. As a result, the attitude indication device of the present invention becomes practical for the detection of egress or attempted ambulation within a medical environment. It will be appreciated that in situations of attempted egress, the thigh of the individual, upon being lowered toward the ground, will typically transition through the slight to moderate downward angles readily, such that downward threshold angle 38 should occur within one or two seconds of transitioning through the slight downward angles.

In other embodiments, the device may be attached to the individual's head, neck, shoulder, arm, chest, abdomen, waist, lower back, calf, or any other body part consistent with its intended use. The device may be attached to the individual using any of the means familiar to those skilled in the art.

Figure 4:
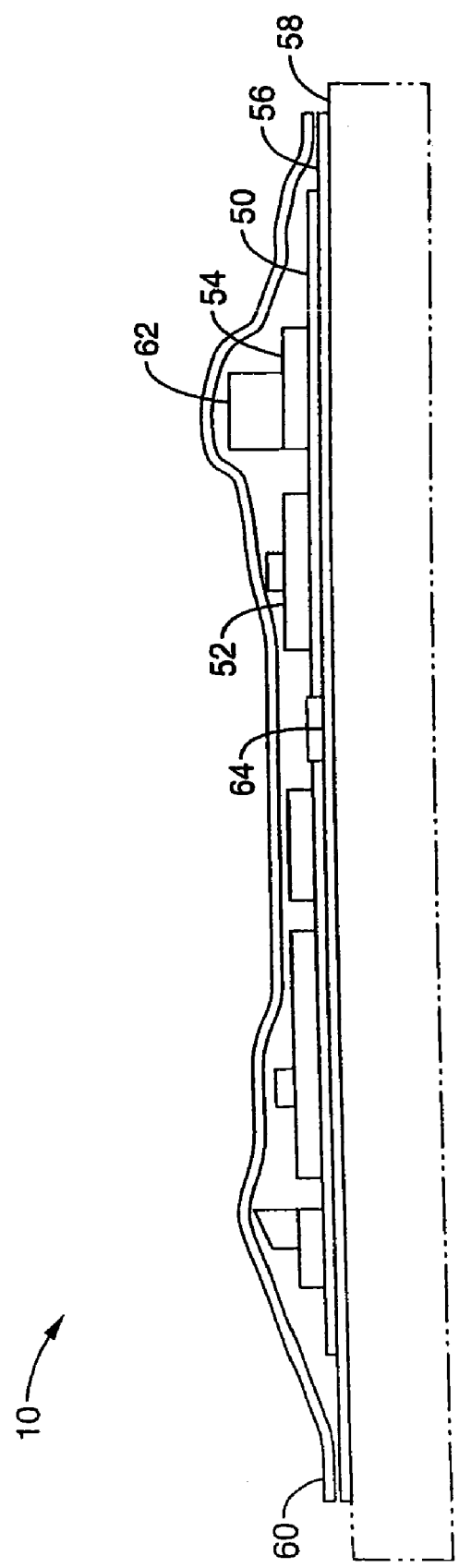
FIG. 4 is a cross-sectional view of an attitude transmitter unit according to the present invention shown integrated within a moisture sealed adhesive medical appliance which is being retained adjacent the skin of an individual.

Referring to FIG. 4, the attitude transmitter unit 10 is sealed and then adhesively attached to the individual, such as on the posterior thigh. The attitude transmitter unit is preferably adapted into a medical appliance that is both waterproof and shockproof; whereby individuals may shower, bathe, or perform additional common tasks over an interval that may exceed one or more weeks without needing to remove the device. The circuitry of the attitude transmitter unit may be sealed by various means that may be used singly or in combinations thereof, and is inclusive of potting compounds, sealants, encapsulation, pouches, or material overlays. It will be further appreciated that other moisture resistant packaging may be utilized, such as implementing the device with high levels of integration, preferably single chip, coupled with the use of waterproof connections.

Attitude transmitter unit 10 of FIG. 4 is shown having a printed circuit board 50 upon which are mounted several electronic components, such as integrated circuit 52. The circuit of the device is preferably sealed against moisture, such as with an insulating sealer 54 applied to the portions of the circuit that require environmental protection.

To create a medical appliance, the transmitter unit may be attached to a bottom adhesive layer 56, such as 9776 Foam Medical Tape™ produced by 3M™, for attachment to the skin 58 of an individual and covered by a top layer 60 of material. It is advantageous if the bottom adhesive layer 56 is fabricated of a material that is capable of maintaining skin adhesion for a period of days, or weeks, and is not subject to a loss of adherence as a result of bathing or similar normal activities. If longer monitoring is required, the tape may be replaced, or a reinforcing band (e.g., Coban™ wrap by 3M™) may be employed. Where no adhesive contact is desirable, the attitude transmitter unit may be attached by means of an Ace bandage™ or the like. However, in the preferred adhesive backed configuration, the adherence of bottom adhesive layer 56 to the skin should still allow for controlled removal from an individual without undue discomfort. The top layer 60 of material should then be applied over the circuit board 50 and circuits 52, so that the perimeter provides an outer seal in connection with bottom layer 56. Top layer 60 may comprise any of various materials, such as 9776 Foam Medical Tape™.

If a transparent region within top layer 60 is desired, such as to facilitate viewing of on-board indicators or information printed on the transmitter unit, then a top layer with a transparent window may be fabricated, for example from a layer of Avery™ Medical 5020 Urethane Tape™ over which is placed a second layer of opaque material, such as foam tape that may be configured with apertures, or as a frame, for viewing.

Optional temperature sensors are shown attached to the circuit board 50, which is shown configured with an outer sensor 62 and inner sensor 64. The temperature sensors can provide additional patient related statistics, while the use of dual sensors further provides for detecting temperature differentials indicative of attitude transmitter patch removal.

Figure 5:
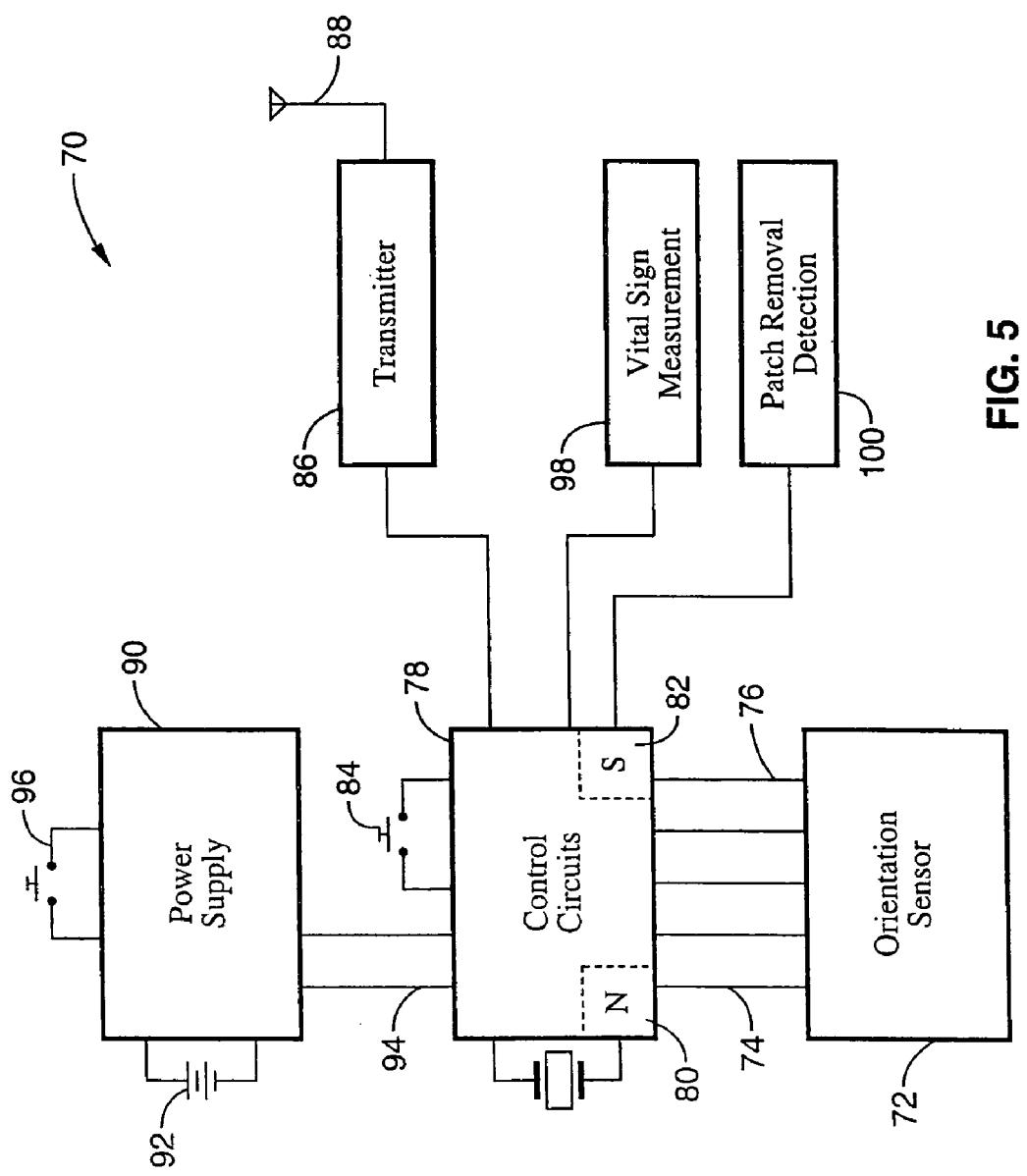
FIG. 5 is a block diagram of a wireless transmitter according to an embodiment of the present invention shown with optional vital sign measurement sensors and patch removal detection circuits.

In FIG. 5 an embodiment and attitude transmitter unit 70 is generally shown comprising an orientation sensor, a controller, an RF transmitter, and a power supply. It will be appreciated that various receivers can be implemented for receiving the signals from the device and for the subsequent display and/or annunciating of corresponding information and alerts.

An orientation sensor 72 is capable of sensing the orientation of the portion of an individual's body to which it is attached. Subject orientation is sensed in relation to the downward force of gravity and may be sensed as an acceleration, inclination, tilt, roll, or similar force that is indicative of orientation for that portion of the individual to which it is attached. The output of the orientation sensor should be largely immune to influence from nearby circuitry, mechanical oscillation, and sensor inertia.

The orientation sensor is preferably capable of sensing from one to three dimensions of orientation, the larger number of axes being used to increase event discrimination, reduce false triggering, and facilitate more complex attitude monitoring applications. In addition, the orientation sensor in combination with the circuit should provide substantially linear output in response to orientation and be configured to dampen transient responses that could otherwise lead to false triggering. The use, therefore, of mechanical position switches is not preferred within the present invention because of their step-wise output and the significant debouncing (in hardware or software) required before the output can be utilized.

The orientation sensor 72 in a preferable configuration comprises an acceleration sensor having corresponding outputs 74. The incorporation of an acceleration sensor provides numerous advantages, which include the ability to sense static orientation in relation to gravity and the simultaneous ability to sense the changes in movement rates, so that subject activities may be accurately discriminated to provide improved differentiation of events to reduce false alarms. If the orientation sensor draws significant amounts of operating current, the circuit should be configured to periodically shut down the sensor, so as to conserve the power source of the portable transmitter. A sleep input line 76 is shown connected to the orientation sensor 72.

Any of various control circuits 78 may be utilized for controlling circuit operation within the attitude transmitter unit. By way of example, the control circuit may utilize any combination of circuitry including application-specific integrated circuits (ASICs), semi-custom integrated circuits (ICs), programmable logic arrays (PLAs), gate arrays, microcontrollers, microprocessors, neural net circuits and assorted discrete circuits. The control circuit 78 coordinates the activities of the orientation sensor 72 and the generation of the output signal, while it can additionally provide for signal processing, event differentiation, the maintenance of event history to provide improved differentiation, signal transmitter control, coordination of auxiliary functions such as temperature measurement, patch removal detection, on/off control, and so forth.

The control circuit 78 is preferably implemented as a low-cost, low-power integrated microcontroller that is capable of performing extended levels of processing on the input signals and of generating complex outputs. The microcontroller may also be serialized with an included identification number 80 which can be decoded by a remote attitude receiver unit for discerning one attitude transmitter unit from another. In addition, numerous microcontrollers provide low-power/sleep circuits 82 which allow the processor itself to enter a low power mode, and to return to conventional power mode upon the detection of an event or upon the expiration of a time interval. Use of a microcontroller as the control circuit provides the additional advantage that attitude detection devices may be custom programmed for specific applications, while the program itself may be periodically updated to include new system enhancements. For example, attitude transmitter units may be custom programmed for various inclination thresholds to suit a variety of applications, such as detecting slight movements of a postoperative or comatose patient.

An optional switch 84 connected to the control circuit 78 provides an activation signal, or wakeup signal, which is responsive to the orientation of the transmitter patch and can provide for further reductions in power dissipation. Switch 84, for example, may comprise a tilt sensor whose contacts change state when subject to a slight angle, such as a tilt exceeding approximately twenty degrees from the horizontal. The tilt sensor in this situation senses that the patient is no longer in a quiescent, non-inclined state. It will be appreciated that if the patient is not moving enough to trigger the tilt sensor, then attitude readings need not be taken and power savings may be accrued by shutting down the orientation sensor 72 and the control circuit 78. Alternatively, a variety of mechanical vibration or pendulum-style devices may be utilized to sense a quiescent state, and/or a non-tilting state, so as to condition the processor and/or the associated orientation sensor into a desired operating mode.

A mechanical inclination switch, such as a series 0732 On/Off switch produced by the Fredericks Company™ of Huntington Valley, Pa., is one example of a tilt switch that may be utilized to condition the operating mode of the transmitter unit. The switch angle between "off" and "on" is configured so that at zero degrees inclination the switch is "off" (non-conductive), and at a tilt angle in excess of twenty-two degrees the switch is activated to an "on" state (conductive).

A mechanical switch does not provide a linear output for accurately detecting attitude; however, it may be safely utilized to awaken the circuitry from a low power mode upon the occurrence of a prospective event. It will be further appreciated that a simple tilt sensor does not have the specificity to distinguish pitch from roll, and as a result the orientation sensor may remain activated with a concomitant level of power dissipation. It is anticipated that an individual, such as a medical patient, shall spend a far greater percentage of their time in a lying position, or a sitting position, therefore, operation of the orientation sensor while a patient lies on one side should not substantially reduce the longevity of the power source within the attitude transmitter unit. Should a reduction in power dissipation be desired for individuals positioned on their side, multiple switches may be utilized in combination to provide axis-selective awakening.

The control circuit 72 is operably connected to an RF transmitter circuit 86 whose output is coupled through an antenna 88. Although other forms of transmissions may be utilized for communication with the remote device, the advantages and simplicity of radio-frequency (RF) transmission make it the preferred form of transmission. The RF transmitter 86 may be constructed from various off-the-shelf RF modules, or from discrete components.

In another aspect of the present invention, a periodic ALIVE signal is broadcast from the device to the remote receiver. The ALIVE signal provides assurance that the associated transmitter is operational and within the range of the receiver. During operation, the ALIVE signal will be periodically generated if the transmitter has not otherwise generated a signal within the given time interval. The associated receiver thereby anticipates, and is conditioned upon the receipt of a periodic signal, which may consist of a measurement, an alert, or the ALIVE signal. If the signal is not received within a predetermined interval, the receiver generates an alert indicative of a non-responsive attitude transmitter unit. It is further preferable that transmission of the ALIVE signal be conditioned upon obtaining a proper result from a self-test routine so that problems within the transmitter unit may be detected by the remote receiver as a fault indication or missing ALIVE signal.

A power supply 90 provides conditioned power to the circuitry from battery 92 such as a lithium battery. The preferred use of power conditioning circuitry, in contrast to the direct connection of battery 92 to the circuitry, provides a regulated circuit supply voltage to maintain unit accuracy, while it additionally provides for the detection and control of power drain from the battery source. The power supply includes a regulator that controls the output voltage for the circuit, and preferably provides a low battery signal 94 to the control circuit. In response to the low battery signal, the control circuit generates an alert to the remote attitude receiver unit that provides an audible or visual indication to personnel so that battery replacement may be initiated.

A momentary switch 96 is shown on the power supply to control the application of power to the device. The switch is preferably implemented to engage and latch power to the transmitter unit while providing security from inadvertent engagement. The optional switch may be implemented in a variety of forms, or left off altogether with circuit activation being contingent upon insertion of the battery into the battery holder of the transmitter unit. By way of example, another form of activation switch can be configured utilizing a magnetically sensitive bi-stable switch, wherein proximal application of a sufficient magnetic field causes the switch to change states. Utilizing the push-button style momentary switch 96, as shown in FIG. 5, provides compatibility with the preferably sealed nature of the device. The momentary switch 96 may be used in concert with the microcontroller in a power activation loop, wherein the momentary switch is pressed for a period of time to exceed the activation loop period in order that power is latched into a permanent "On" state. Alternatively, the state of power activation may be controlled within a properly configured device by means of a radio transmitter, infrared source, or similar signal.

The attitude detector may be optionally configured with sensors 98 to register one or more vital signs of the individual, for example temperature, heart rate, and/or blood pressure. Although, the attitude indicator provides for the detection of the physiological attitude of a portion of an individual, it may in addition provide for the communication of an individual's vital statistics, or the generation of alerts based on those vital statistics, to facilitate directing proper attention to those individuals in distress or possible danger.

Furthermore, the transmitter unit preferably is configured with a detector 100 that is responsive to the removal of the patch from the individual. The appliance containing the attitude indicator may become separated from the patient if the retention mechanism, such as the adhesive layer, which holds the appliance to the patient's body fails, or if the patient accidentally or purposely removes the appliance. First, it should be appreciated that a preferred embodiment utilizing an acceleration sensor can be configured to monitor acceleration conditions which are indicative of not only the orientation, but of events relevant to the status of the device, such as monitoring for device removal. It will be recognized that the device, during and after removal, is subject to increased levels of acceleration, and fluctuations thereof, due to its minimal mass in comparison to the mass of an individual's thigh to which it is preferably retained. Therefore, events experienced by the detector upon or after removal, such as being dropped or jarred, may be sensed and differentiated from events taking place when the attitude transmitter unit remains attached to an individual. However, the use of an additional sensor configured specifically to sense attitude transmitter patch removal is preferable, so that transmitter patch removal may be detected under all circumstances.

In one removal detection aspect, a temperature sensor may be utilized to sense patch removal, as the temperature of the surroundings is generally lower than skin temperature, whereby a drop in temperature is characteristic of device removal. However, the combination of two temperature sensors is preferred, with one near the exterior of the patch and one near the interior of the patch to improve patch removal detection based on a temperature differential. The combination of acceleration sensing and patch removal detection can provide an extremely accurate and rapid removal detection mechanism, such that a responsive action may be quickly taken. It will be appreciated that sensors that operate according to any of various operating principles may be utilized within the present invention to detect the removal of the transmitter from the individual. By way of example, a pair of differential humidity sensors could be utilized instead, with an inner humidity sensor generating a higher level of humidity than the outside sensor while the attitude indicator remains attached to the individual.

Alternative detection mechanisms include monitoring for conductivity changes that are characteristic of the transmitter being removed from the patient. Conductivity may be measured between electrodes placed proximal to the skin of the wearer. Alternative mechanisms may be utilized for sensing characteristics associated with device removal, such as changes in applied pressure, inductance changes, capacitance changes, in addition to further mechanisms capable of sensing the removal of the attitude detector from the individual.

Figure 6A:
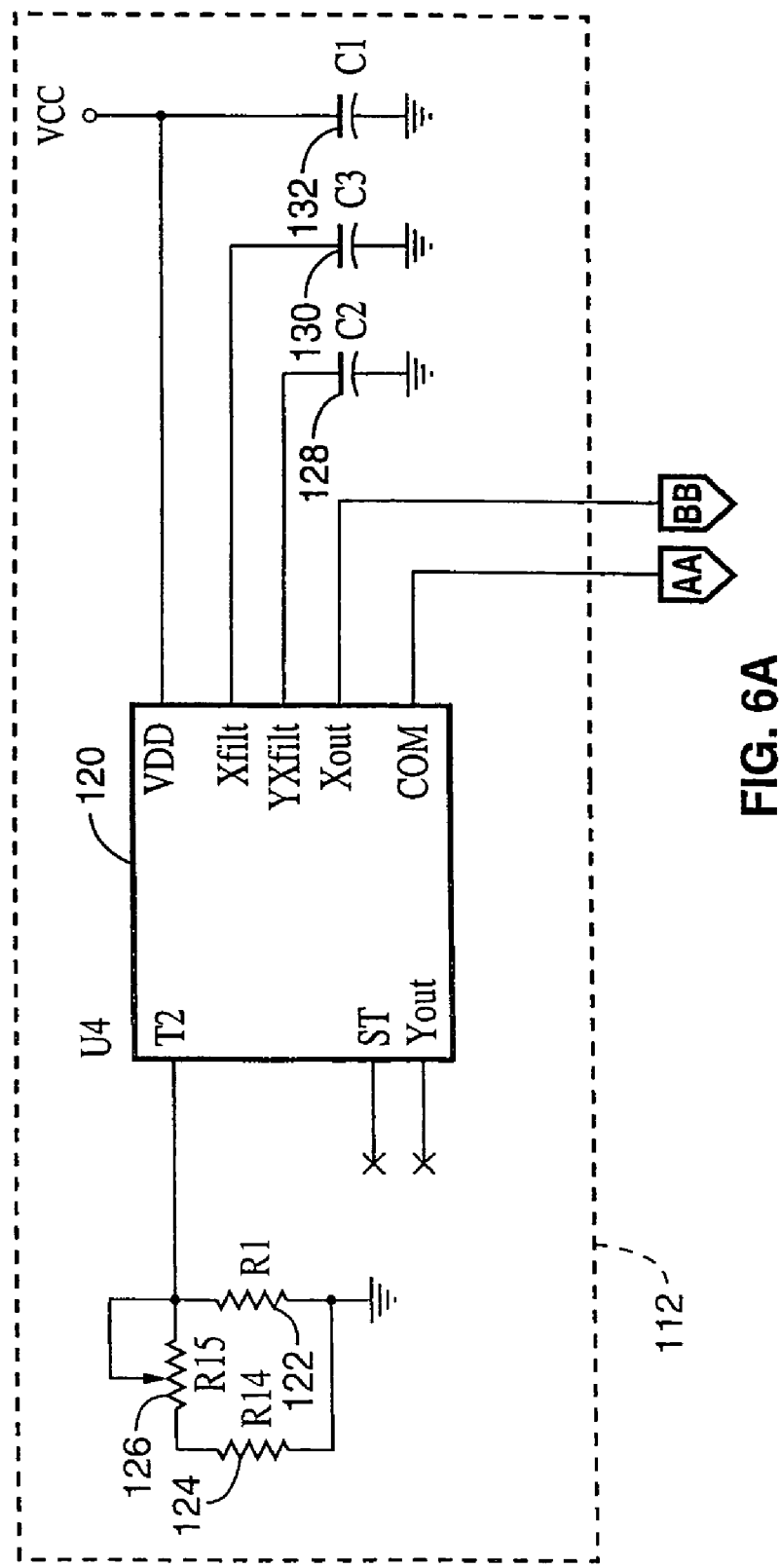
FIG. 6A is a schematic of an orientation sensor circuit within a wireless attitude transmitter unit according to another embodiment of the present invention shown for transmitting single axis orientation alerts that are configured for reception by a remote indication device.
Figure 6B:
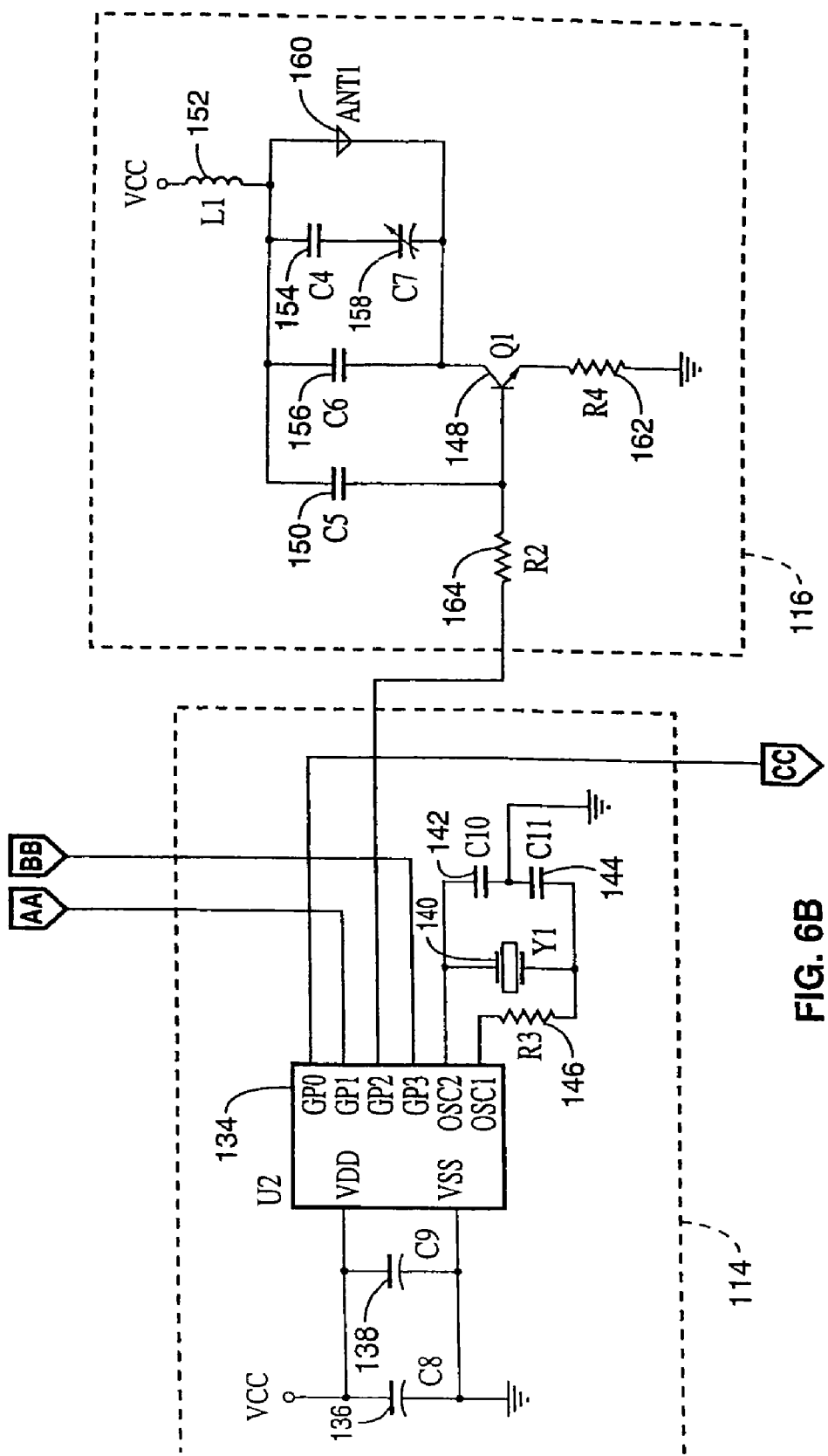
FIG. 6B is a schematic of a control circuit and RF transmitter within the wireless attitude transmitter unit associated with FIG. 6A.
Figure 6C:
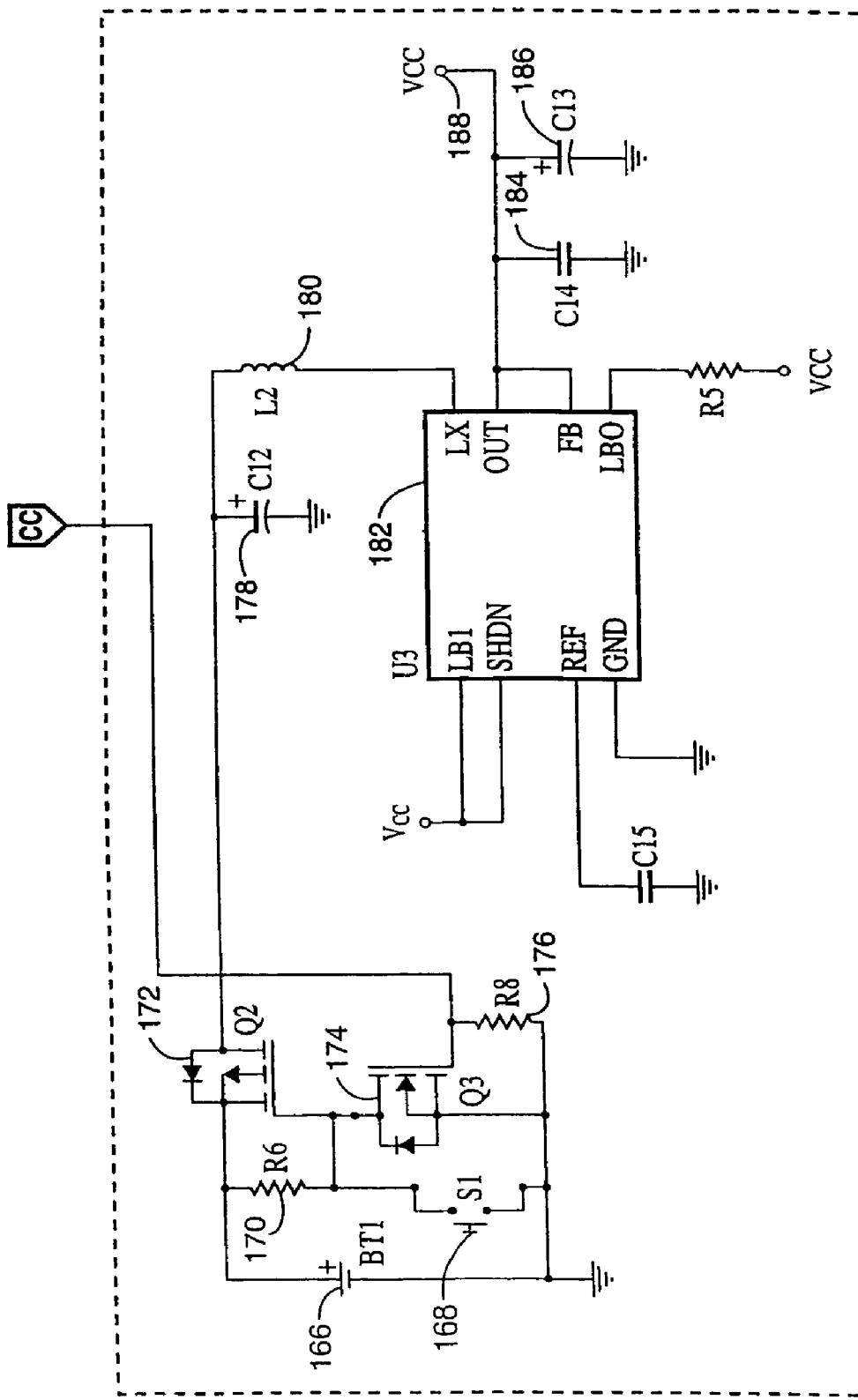
FIG. 6C is a schematic of a power control and power supply circuit within the wireless attitude transmitter unit associated with FIG. 6A.

Referring now to FIG. 6A through FIG. 6C, a circuit for another embodiment of the attitude transmitter unit is shown. In this embodiment, the attitude transmitter unit is worn by an individual, preferably against the skin as a medical appliance, or transmitter patch, wherein attitude related information is transmitted from the attitude transmitter unit to a remote receiver. Transmitter range is configured for approximately fifty feet as measured in an open room and the range is independent of relative orientation between the transmitter and its respective receiver. The range of the transmitter may be alternatively adapted to suit other applications, the fifty-foot range being provided by way of example based on testing of the attitude indication device utilized as an egress detector within a room containing a single receiver.

Preferably, an ALIVE signal is sent from the attitude transmitter unit to the attitude receiver unit approximately every one to ten minutes, so that the remote receiver unit can detect if the attitude transmitter unit is positioned out of range or is no longer serviceable. Operational life of the transmitter battery was found to exceed one week under circumstances in which the attitude transmitter unit was exposed to twenty, or fewer, minutes per day in an alert generating state, e.g., positioned vertically. An alert signal is generated by the attitude transmitter unit as it detects a possible patient egress condition triggered by a downward pitch of the device exceeding about seventy degrees from the horizontal. The embodied single axis transmitter is insensitive to patient roll and therefore does not generate alert signals when the patient shifts to a position lying on their side or raises a leg toward the ceiling instead of the floor.

The attitude indicating device of FIG. 6A through FIG. 6C for detecting patient egress can be broken down into four major sections: orientation sensor circuit 112 of FIG. 6A, microcontroller circuit 114 and RF transmitter circuit 116 of FIG. 6B, and the power supply circuit 118 of FIG. 6C. Table 1 contains a list of the components utilized within the exemplified embodiment.

In FIG. 6A the orientation sensor circuit 112 within the attitude indication device is shown as being implemented using an ADXL202E acceleration sensor (U4) 120 from Analog Devices™. Two axis outputs are provided, with the X-axis being utilized within the attitude transmitter unit for measuring tilt, while the second output, if used, corresponds to the measurement of roll. Each of the two outputs from acceleration sensor 120 is independent and directly proportional to the acceleration in each of the two sensitive axes. The outputs are pulse-width modulated (PWM), wherein continuous pulse trains are generated in which the duty cycles represent the present level of acceleration to which the sensor is subject. Only a single channel of the acceleration sensor is utilized for sensing the tilt within this particular embodiment to which the portion of the body upon which it has been attached is subjected.

The operation of the acceleration sensor 120 shown in FIG. 6A is herein controlled by three components associated with the ADXL202E. The first component R1 is a resistor 122 that in combination with a parallel resistance comprising a fixed resistor R14 124 in series with an adjustable resistor R15 126, sets the output periods of both tilt and roll for the acceleration sensor, which is preferably adjusted to yield a square wave output having a period T2 ranging from approximately one-half to one millisecond.

A pair of capacitors, C2 128 and C3 130, is utilized as filter capacitors by the ADXL202E to establish the bandwidth of the acceleration sensor. The duty cycle of either axis for the acceleration sensor is approximately fifty-percent when no gravity force is being registered within that axis, and the duty cycle changes by approximately twelve-point-five percent per gravitation unit (G). The acceleration sensor bandwidth determines the maximum measurement resolution that thereby defines the smallest detectable acceleration change. In the present circuit, capacitors C2 128, and C3 130 are set to provide a resolution of approximately fifty Hertz. The supply voltage $V_{cc}$ is bypassed by a capacitor C1 132. The X output of the accelerometer is connected directly to the microcontroller circuit 114 that determines acceleration based on the duty cycle of the received PWM square wave.

In FIG. 6B, the microcontroller circuit 114 contains a PIC12C508 eight-bit, eight-pin microcontroller chip U2 134 from Microchip Semiconductor™ which provides low power consumption, internal peripherals, a counter/timer with prescaler, 25 bytes of RAM memory, and 512 bytes of non-volatile (program) memory. The microcontroller 134 within the depicted embodiment performs reading and interpretation of accelerometer output signals, the latching of circuit power, the control of power to the acceleration sensor, and the modulation of the RF transmitter with data to be transmitted to the remote attitude receiver unit.

Although other forms of control circuits may be utilized, the use of a microcontroller 134 within the attitude transmitter unit provides significant advantages over the use of simple thresholding circuits. By way of example, the microcontroller is capable of complex circuit control and of performing simple signal processing functions that for instance utilize historical signal information so that the number of false alarms may be reduced.

In addition, the firmware programming of the microcontroller may be adapted to suit different applications of the sensor, and to accept firmware updates thereupon. Microcontroller 134 may be programmed with various firmware settings and operating features to support a wide range of alert configuration and applications. For example, the firmware may be programmed to detect a declination other than seventy degrees, or the tilt may be qualified with additional metrics to suit other applications. When the transmitter unit is to be utilized within applications that are subject to change, such as a change in parameters or programming, the microcontroller should preferably be reprogrammable (for example, utilizing FLASH ROM) and be configured to receive off-board programming signals to allow for the updating of firmware.

The microcontroller 134 receives a single axis input from the acceleration sensor 120 on general-purpose I/O pin GP3 and outputs a single bit from I/O pin GP2 to modulate the RF transmitter circuit 116. The microcontroller circuit 114 additionally provides an output GP0 for latching the battery power for the device, while I/O pin GP1 is utilized for controlling the operational state of acceleration sensor 120. The microcontroller must configure GP1 into a Low state output capable of sinking operating current from the acceleration sensor to thereby activate the sensor. A pair of bypass capacitors C8 136 and C9 138 is provided to filter voltage transients created by microcontroller 134. The frequency of oscillation within microcontroller 134 is established by quartz crystal Y1 140 that is configured with a pair of capacitors C10 142 and C11 144 and an overdrive-limiting resistor R3 146.

The control and operational characteristics of the attitude indication device of the depicted embodiment of the present invention are preferably embedded within the microcontroller firmware. In addition, it is preferable that the individual microcontroller chips within individual attitude transmitter units be configured, or programmed, with a unique identification code that may be utilized by the firmware for encoding an identifier within the RF output so that individual attitude indication devices may be distinguished from one another.

The redio-frequency (RF) transmitter circuit 116 provides a pulse code modulated (PCM) transmitter that receives data input from the microcontroller circuit 114. In the exemplified embodiment, a broadcast signal of approximately 302 MHx is generated through an RF switching transistor Q1 148, feedback capacitor C5 150, an inductive choke L1 152 and LC tank circuit comprising capacitors C6 156 in parallel with series combination C4 154 and C7 158, which is in parallel with antenna ANT1 160 that is configured as a trace on the printed circuit board (PCB). It will be appreciated that a wide variety of discrete and modular RF transmitter circuits may be alternatively utilized within the present invention, with the choice being dependent on factors including cost, range, selectivity, desired operating frequency, data rate, application, and environment.

The antenna ANT1 160 is implemented as a PCB trace that is 100 millimeters thick and is configured in a rectangular form factor to reduce the requisite area of the printed circuit board (PCB), although antenna geometry is not critical due to the short-distance over which the data is to be communicated and the low data rate involved. An LC tank circuit generates the 302 MHz oscillation signal, with inductive choke L1 152 providing an AC blocking choke that provides power to the oscillator. The inductor, choke L1 152 in addition prevents the AC component of the oscillator from entering the DC supply unattenuated. The antenna acts as the "L" in the LC tank circuit, with the "C" comprising the parallel-serial combination of C4, C7 and C6. This configuration helps offset the PCB parasitic capacitance and allows for fine-tuning of the transmission frequency.

A high-frequency NPN transistor with a gain bandwidth product of 10 GHz is utilized for the RF switching transistor Q1 148, rated for a maximum collector current of 35 mA which is limited by emitter resistor R4 162. The transistor Q1 148 provides a high-frequency switching device which is modulated by the microcontroller circuit 114 and which receives positive feedback from the tank circuit through capacitor C5 150 to maintain oscillation.

The base of transistor Q1 148 is modulated through a drive resistor R2 164 by an output from microcontroller 134 which switches the RF transistor Q1 148 on and off in response to the binary pattern of data being transmitted. During the "on" period of the transistor, collector current flows and initially puts the transistor into saturation which in turn charges up the capacitors C4 154, C6 156, and C7 158 and prepares the capacitors for energy exchange with the antenna ANT1 160 which acts as an inductor. Conversely, when the base of transistor Q1 148 is held low, the transistor collector current is reduced to allow the LC tank circuit to oscillate with the stored capacitive energy. The feedback component is implemented as a capacitor C5 150 that provides positive feedback to the base of RF switching transistor Q1 148, which in turn allows the tank circuit to continue to oscillate at the desired frequency of 302 MHz.

In FIG. 6C, the power supply circuit 118 is responsible for supplying the attitude transmitter unit with a source of regulated power exemplified as a standard 3-Volt button cell lithium battery BT1 166 with a preferred capacity in the vicinity of 560 mAH. The battery BT1 166 is switched in and out of the circuit by a push-button normally-open (PBNO) switch S1 168 which acts in concert with the microcontroller 134 to control pass element 172 which switches battery current on or off. From a steady state inactive mode of the circuit, such as when the battery is initially connected to the circuit, pressing switch S1 168 causes current to be drawn through resistor R6 170 thus pulling the gate of MOS FET transistor Q2 172 to ground, thereby activating it and providing power to the remainder of the circuit.

With the push-button still engaged, microcontroller 134 transitions from a reset state to begin executing firmware instructions. One such instruction generates an output on GPO of microcontroller 134 which activates MOS FET Q3 174, normally pulled inactive by resistor R8 176, to thereby sustain the activation of MOS FET Q2 172 after switch S1 168 is released. It will be appreciated that the firmware instructions may latch the power to the circuit after any programmed period of time has elapsed following device reset. It is preferred, however, that the microcontroller latch the power on after a period of about five seconds such that inadvertent momentary activations of the power switch do not cause the device to enter an active state. Subsequent engagements of switch S1 168 have no effect on circuit power once it is latched into a power activated mode.

Current for the circuit passes through MOS FET Q2 172 from battery BT1 166 to a voltage converter and/or voltage regulator U3 182 through a power filter that may be exemplified as a tantalum bypass capacitor C12 178 and a series inductor L2 180. The voltage converter/regulator U3 182 of the present invention is exemplified with a step-up DC-to-DC converter so that a single battery may be utilized to supply a regulated supply voltage to the entire circuit. The step-up converter U3 182 shown is a MAX1675 step up DC-DC converter configured to output 3.3 volts. The step-up converter additionally provides a low battery indication LBI output, which detects a low battery condition that may be utilized in additional embodiments of the transmitter unit so that caregivers may be alerted to the need to replace the battery. The output of the voltage converter U3 182 is subsequently filtered by capacitors C14 184 and C13 186 which supply the regulated $V_{cc}$ voltage 188 to the circuitry.

The attitude transmitter unit exemplified in FIG. 6A through FIG. 6C was configured according to the invention to provide a reliable, yet simple and inexpensive transmitter for detecting attempted egress of an individual when not subject to immediate or direct supervision. The attitude transmitter unit is preferably attached to the posterior thigh of the individual being monitored, as previously described.

After device power is activated and the microcontroller starts processing firmware instructions, the orientation information provided by the acceleration sensor is monitored for a transition that is characteristic of a downward inclination of the acceleration sensor upon the thigh of the patient to a downward angle that exceeds seventy degrees from the horizontal.

It will be appreciated that by monitoring a single axis of motion, the exemplified device is insensitive to movement in the other two planes of motion for this particular application. When measurements from the acceleration sensor indicate that the seventy-degree threshold has been exceeded, the microcontroller outputs data for transmission to the remote attitude receiver unit via the RF section of the circuit. The RF transmission is configured for receipt by a remote attitude receiver unit (not shown) that is capable of indicating the alert condition by the use of indicators, displays, audio annunciators, and/or communications to additional circuitry that is capable of directly, or indirectly, indicating the alert condition.

A number of procedures are utilized within the attitude transmitter device to reduce the overall power consumption so as to increase the interval over which the unit may be utilized between battery replacements. First, the power for the acceleration sensor is under the control of the microcontroller that is capable of cycling the power to the acceleration sensor as attitude measurements are necessary. It will be appreciated that the thigh of an individual upon which the device is attached contains a mass that will not allow it to transition from being horizontal to an inclination that exceeds the downward threshold in a short span of a few milliseconds, and that the amount of time required to move to the position where the threshold is exceeded depends upon the present downward angle. It should additionally be recognized that the determination of a downward angle exceeding the threshold need not be registered instantly; a delay of up to one second for human applications would generally be considered insignificant. Therefore, the firmware of the microcontroller selectively activates the acceleration sensor in response to the last known angular position.

To further conserve battery power, the microcontroller can put itself into a sleep mode wherein the microcontroller enters a low power mode until a specified period of time has elapsed, and in so doing effectively "naps" during periods of low activity, and/or low angles of thigh inclination. However, the attitude transmitter device will transmit a periodic ALIVE signal to the receiver irrespective of the downward angle threshold, such that proper operation of the attitude transmitter is continually being verified.

Figure 7:
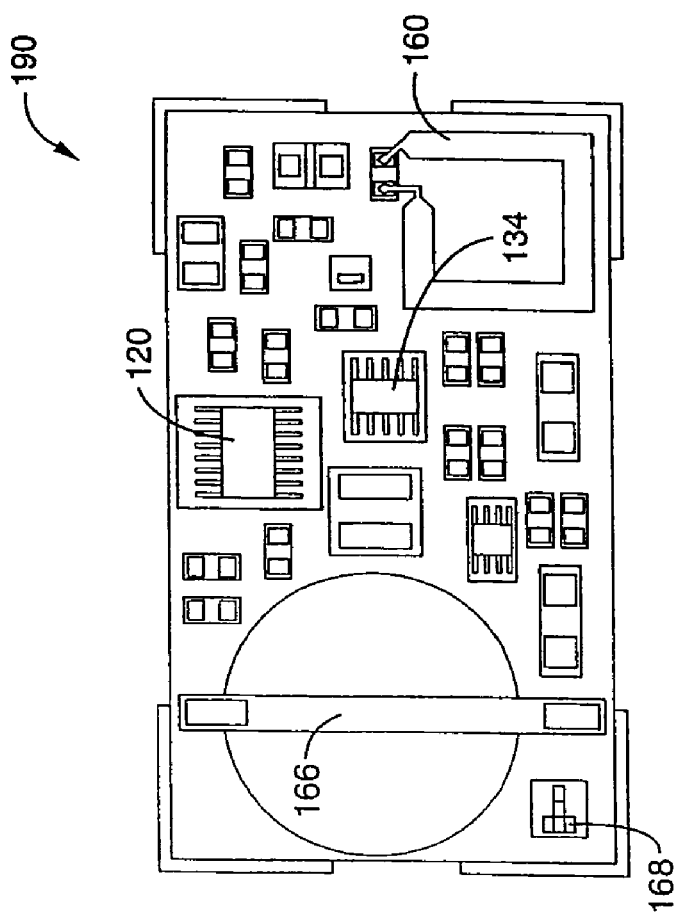
FIG. 7 is a plan view of a printed wired assembly for an attitude transmitter unit, according to the schematic of FIG. 6A through FIG. 6C depicting component placement.

FIG. 7 exemplifies a printed wired assembly for the attitude transmitter unit shown in FIG. 6A through FIG. 6C. Apparent on the printed wired assembly 190 are the lithium battery 166, the trace of the loop antenna 160, the acceleration sensor 120, the microcontroller 134, and the momentary switch 168, in addition to the various aforementioned discrete circuit components. The attitude transmitter unit is fabricated as a small, lightweight device that is preferably attached to the posterior thigh of an individual whose positional attitude is to be monitored, such as for detection of egress. The attitude transmitter is implemented for inclusion within a small patch to create a medical appliance which may be worn for extended periods and which may be disposed of as conventional hospital waste. The electronic circuits of the device are soldered, primarily as surface mounted devices, to a printed circuit board (PCB), herein having dimensions of 2.4 inches in length, and 1.375 inches in width, with a height of about 0.2 inches that is largely determined by specific component packaging.

The attitude transmitter unit is fabricated into a package preferably devoid of sharp edges that could injure, or cause discomfort to the individual wearing the unit. In particular, the corners of the PCB have been radiused to 0.125 inches, and the assembled PCB has been potted in a soft elastomer. The elastomer, preferably registering under 60 on a durometer with the Shore A scale, is utilized to protect the electronics while protecting the wearer from any sharp edges or protrusions within the underlying structure. The elastomer should further be capable of withstanding immersion in 100 degree Fahrenheit water for three hours.

The push-button momentary switch of the device is mounted to allow for activation through the combination of potting layer and adhesive cover. The assembled PCB of the attitude transmitter unit is configured for inclusion within a patch or other medical appliance, and is preferably sandwiched between two sheets, herein provided as 2.5 inches in width by 3.5 inches in length of 3M™ 9776 foam tape™ (or equivalent), with each of the four corners rounded to a 0.5 inch radius. The upper surface of the tape should contain an indicia comprising directions as to which end of the patch is to be oriented toward the feet of the patient, along with additional information regarding the location of the switch, the lot number, the trade name, and any desired trade dress.

The completed patch is preferably individually wrapped in a pouch with an IPA wipe. The pouch itself is marked with trade name, directions for application, indications and contra-indications for use, directions for disposal or reuse, and optional elements of trade dress. The pouch may be configured with a transparent window through which the lot number of the patch may be seen without opening the pouch. During manufacture, the pouch should be exposed to sufficient levels of gamma radiation to ensure sterilization. The packaged attitude transmitter unit is expected to have a useful shelf life of two years when properly stored.

Alerts and information generated by the attitude transmitter device are monitored by an attitude receiver unit that is capable of detecting and interpreting the signals from the attitude transmitter unit, and of generating an indication to personnel as to the status, or alert, which has been communicated. The attitude receiver unit registers the attitude transmissions from the attitude transmitter and is preferably configured to meet the analysis, display, and recordation needs of a particular application. The registration of attitude information comprises reception followed by identification, attitude recognition, or activity characterization, along with displaying, annunciating, or logging the transmitted conditions. It will be further appreciated that the attitude receiver unit may act as a repeater, or transfer node, wherein the signals from the attitude transmitter unit(s) are further communicated to subsequent system elements. For example, the signals may be interfaced with a nurse's monitoring station.

Figure 8:
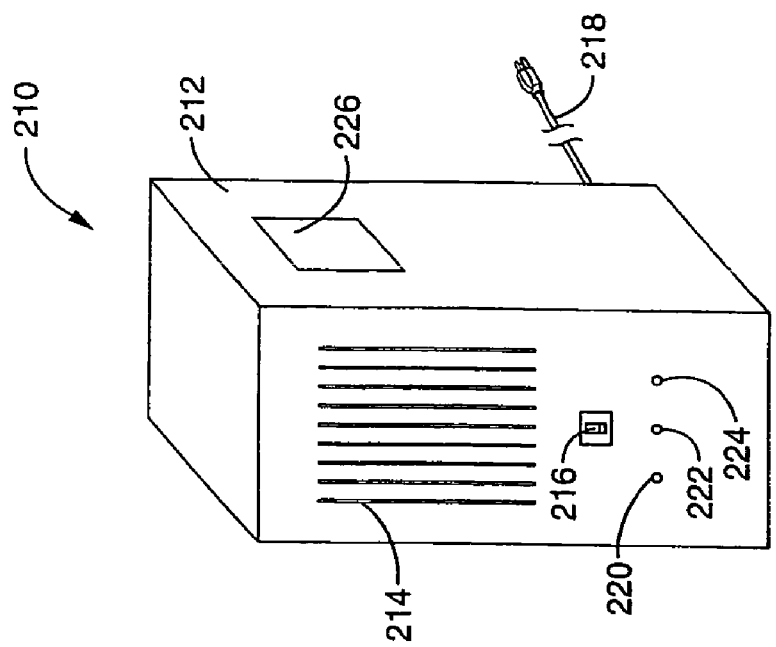
FIG. 8 is a perspective view of an attitude receiver unit that may be utilized according to the present invention.

FIG. 8 exemplifies an attitude receiver unit 210 configured for monitoring a single nearby attitude transmitter unit. The embodied receiver unit 210 is contained within a housing 212 that contains a speaker (not shown) attached behind a speaker grill 214. Annunciations are generated over the speaker by the attitude receiver unit 210 in response to conditions that exist within either the attitude transmitter unit, or the attitude receiver. The annunciations may take the form of various tonal patterns, such as beeps or by way of voiced annunciations that are either computer generated or played from a memory storage device.

Power for the receiver unit 210 is activated with switch 216 with the source of power being either batteries (not shown), or external power that may comprise low voltage, or AC power. If the unit is powered by an external power source, it is preferable that the external power source operate to maintain a charge on an internal storage cell such that the unit may continue to operate for a period of time after the loss of the external power, such as during a power failure.

A connection 218 to AC power is shown, by way of example, for powering receiver unit 210. The status of the receiver unit is indicated by way of status indicators, which are depicted as LEDs positioned on the front of housing 212. A ready LED 220, preferably green, indicates that the receiver is active and capable of receiving signals from the associated attitude transmitter unit. It is preferable that ready LED 220 blinks in response to a loss of external power, or in response to detecting a low battery voltage. A low transmitter battery LED 222, preferably red, indicates that the remaining battery capacity of the associated attitude transmitter unit is low and the battery should thereby be replaced. An ALIVE LED 224 indicates that the ALIVE signal continues to be timely received from the associated attitude transmitter unit. It is preferred that this LED be a Red/Green LED that is activated with current in a first direction to output a steady green illumination when the keep alive signal is properly received, and in response to non-receipt of the ALIVE signal, LED 224 should be activated with intermittent current in an opposing second direction to output flashing red illumination. An access panel 226 is provided to allow access to a set of receiver controls, not shown, which may include volume and specific alarm-related options.

It will be appreciated that the attitude transmitter unit depicted in FIG. 6A through FIG. 6C provides an alert output upon being subjected to a declination that exceeds approximately seventy-degrees from the horizontal. Conventional RF receivers may be utilized to provide an attitude receiver unit that is capable of indicating the attitude condition of the individual as reported by the attitude transmitter unit.

For example, testing of the attitude transmitter unit design was performed utilizing an RS-500 Auto Security Alarm System™ from Radio Shack™, which was modified to (1) remove the motion detector so that an alarm was not generated in response to receiver motion, (2) power the unit from conventional batteries, and (3) diminish the loudness of the alarm. In addition, the antenna wire was removed to desensitize the receiver, because the receiver during these tests was located in the same room as the individual whose positional attitude was being monitored. The receiver without the antenna wire could still be activated by the transmitter from a 75-foot range. The Radio Shack™ receiver and other similar receiver units additionally provide the capability to receive status information, such as the ALIVE signal, and battery status, although upon channels generally designated for other functions. It should be appreciated that the functions of the attitude transmitter unit are best accommodated by a receiver that is specifically designed and configured for indicating alerts from an attitude transmitter unit.

Figure 9:
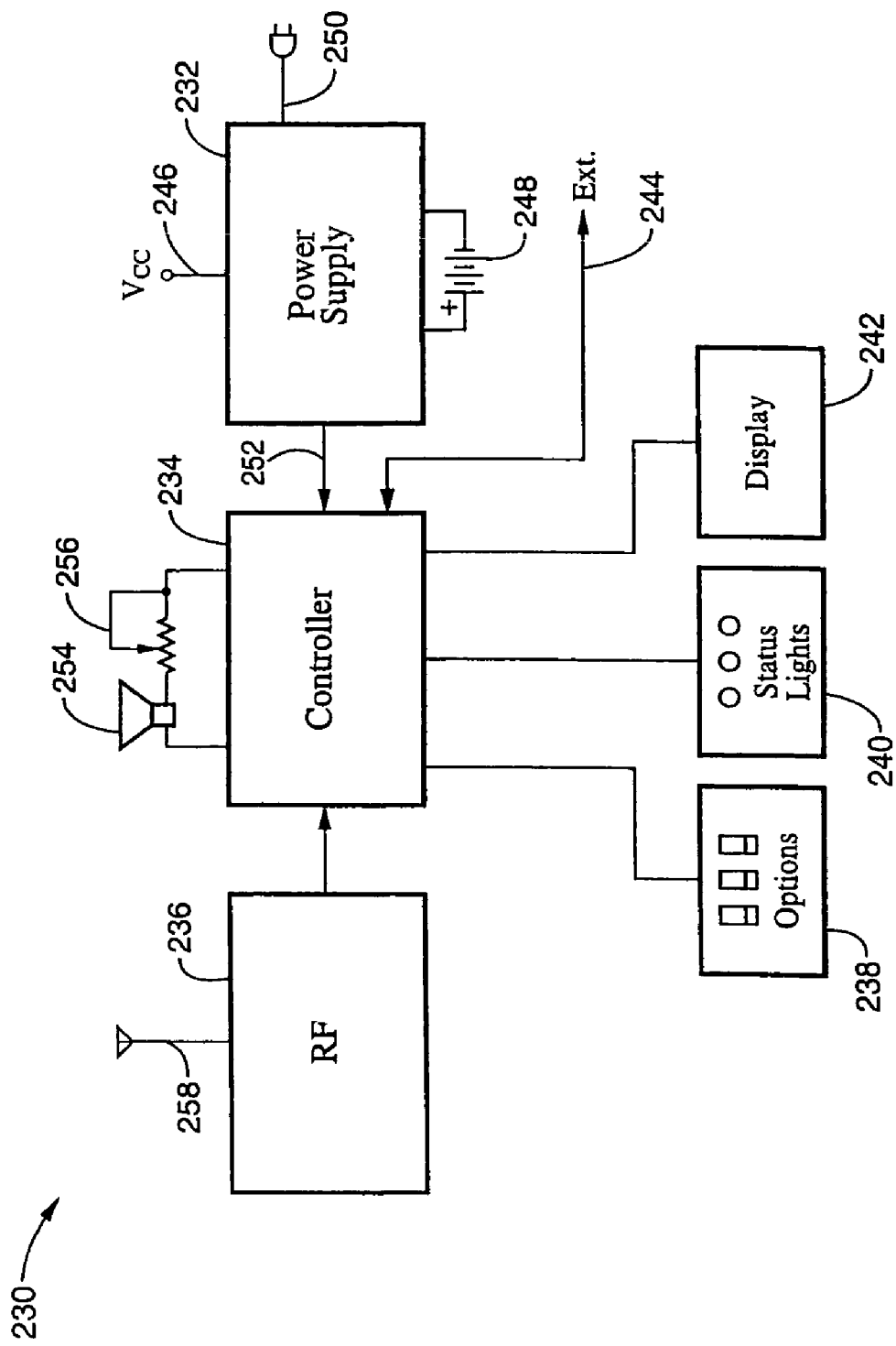
FIG. 9 is a block diagram of an attitude receiver unit according to an embodiment of the present invention shown providing a variety of indicative outputs.

FIG. 9 is an embodiment of an attitude receiver circuit 230 according to the present invention comprising a power supply circuit 232, controller circuit 234, RF receiver circuit 236, option selection inputs 238, status indicators 240, display 242, and an external communications connection 244. The power supply 232 provides the operating voltage 246 for the receiver circuit, and preferably contains, primary or secondary batteries 248, and an optional external power input 250 for maintaining secondary batteries 248 in a proper state of charge. The controller 234, preferably implemented as a microcontroller, manages the operation of the receiver according to the programming of the microcontroller firmware. The controller is capable of audio output through an audio transducer 254, such as a speaker or piezoelectric transducer, whose volume may be adjusted by the potentiometer 256. The controller receives information from one or more attitude transmitter units by way of the RF receiver circuit 236 having antenna 258. The operation of the controller may be set for the specific application, by a set of option inputs 238, which may be implemented as one or more DIP-switches, or any alternative form of input device. The status of the system and attitude transmitter may be displayed on a set of discrete status indicators 240 and/or a text or graphical display device 242. Furthermore, the controller is capable of communicating with additional devices by way of a communication channel 244, which may be implemented as any form of communication channel including but not limited to an embedded system signal, a serial communication channel, an infrared link, an RF link, a network connection, an Internet connection, and so forth. One particularly promising form of communication channel that may be utilized is short-range digital radio, such as embodied within the Bluetooth™ standard. The Bluetooth standard is a layered RF specification that unites computing with communications, and thereby allows the transmitter unit to interface with internet-based receiver units.

The attitude receiver unit is preferably capable of generating indications as received from more than one attitude transmitter unit. Accordingly, transmitter units may be distinguished from one another within the receiver by a variety of mechanisms, including the allocation of separate frequencies, and the inclusion of identification signals within each data transmission of an attitude transmitter. The use of embedded identifiers can allow a simpler RF receiver circuit to be utilized, because the required data bandwidth is exceedingly narrow and the problem of overlapping signals may be readily overcome by configuring the transmitters to repeat a given data transmission a certain number of times with random temporal offsets while including a checksum within each transmission to assure ungarbled receipt.

Operation of the attitude indicator system of the present invention is preferably determined by the firmware contained in the transmitter unit such as shown in FIG. 5 and in the receiver as shown in FIG. 9. The firmware of the microcontroller within the attitude transmitter unit controls the numerous functions that may be performed within the system, including power-on initialization, battery status checking, acceleration sensor signal processing, ALIVE signal processing and generation, patch removal processing, temperature processing, and the transmission of data to a remote receiver.

Figure 10:
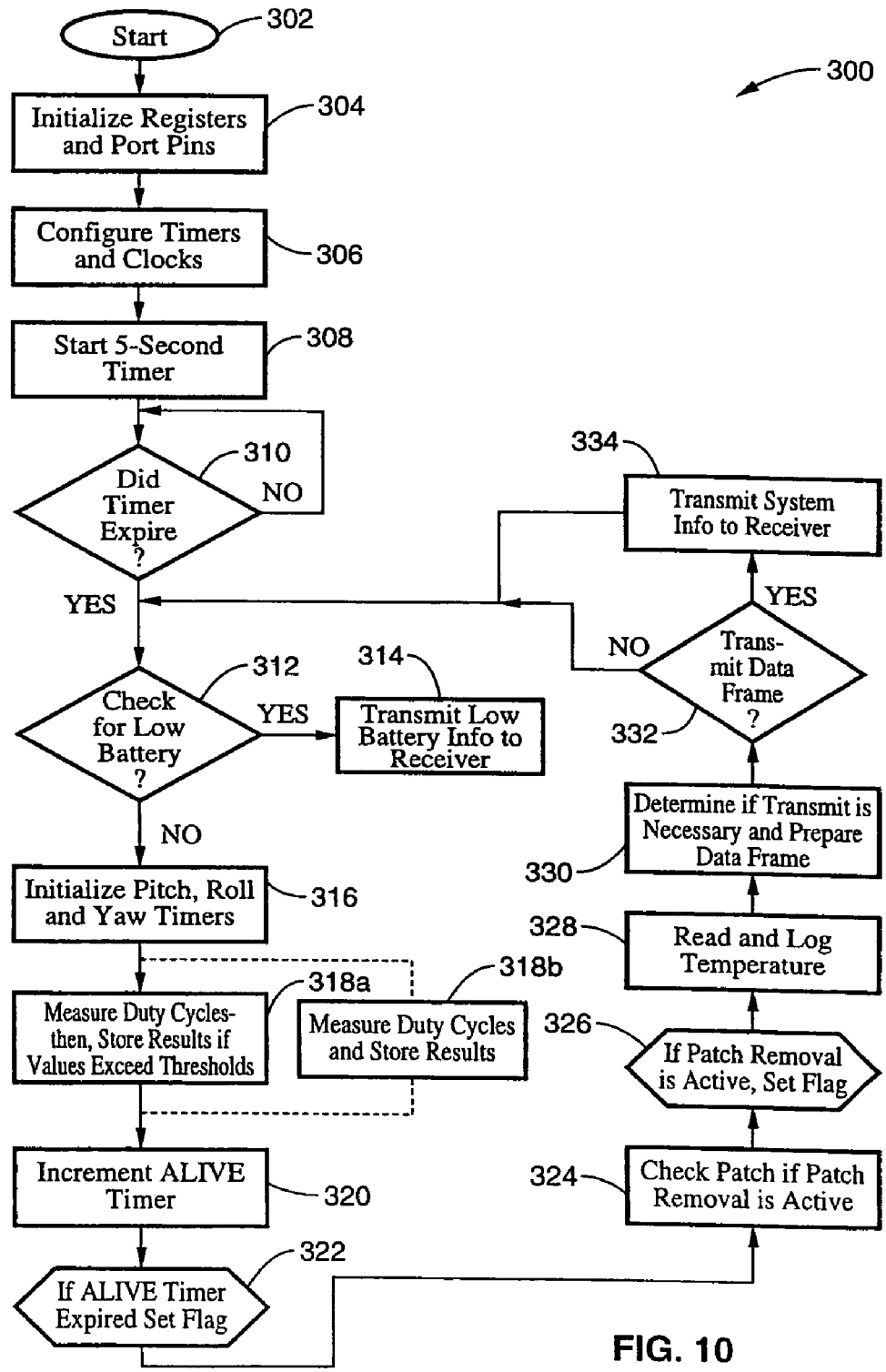
FIG. 10 is a flowchart of program flow within an attitude transmitter unit according to the present invention that exemplifies the process of attitude detection.

FIG. 10 exemplifies process flow 300 within a transmitter unit embodiment of the present invention. The process flow generally describes functionality according to the system depicted in FIG. 5, and contains a superset of functions in relation to the embodiment as shown in FIG. 6A through FIG. 6C. In block 302 the process is entered and the microcontroller, or processor, is powered-up and reset, whereupon it begins executing programmed instructions from firmware at block 304 and initializes both the hardware and microcontroller. Initialization includes setting the modulation signal to the RF section to an inactive state and clearing all timer variables and flags. Timers and clocks are initialized at block 306 and a five-second power-on timer is set at block 308. A delay loop is entered at block 310 pending the expiration of the timer.

The five-second timer is utilized to differentiate an intentional activation of a momentary power-switch from an inadvertent activation. If the user releases the momentary button after holding it activated for less than five seconds, the attitude transmitter unit will return to a powered-off state. If the momentary button is held for greater than five seconds, the controller and power circuit hardware operate in concert to latch the transmitter unit into an active-on state such that power will remain on until the battery is removed or battery voltage drops below that required by either the power supply circuits or microcontroller circuits.

Once attitude transmitter power has been latched to an active-on state, a low battery check is performed at block 312, which additionally provides the entry point for the main loop. It will be appreciated that an infinite variety of software structures may be utilized to support the aforementioned functionality, however, a simple linear program is most readily created comprising an initialization series, blocks 302 through 310, followed by a main loop, blocks 312 through 334, which perform all recurrent processing. If a low battery condition is detected in block 312, a low battery condition is transmitted to the receiver as indicated by block 314. Once a low battery condition has been detected, it is preferably transmitted on a periodic basis until the battery is replaced.

The signals from the orientation sensor, embodied as an acceleration sensor, are processed by first initializing the circuits for each axis, such as the timers utilized for pitch, roll, and/or yaw as shown in block 316. The orientation output is then registered, for instance as pitch, roll, and yaw measurements in either block 318a, or in the alternative block 318b. Block 318a conveys a version of firmware that provides alerts in response to the angular orientation. Block 318b, in contrast, exemplifies the storage of a value in accord with the orientation measurement, so that a measurements may be conveyed, either upon change, request, or periodically, to the remote attitude receiver unit for display. Referring again to block 318a, registered measurements are compared with predetermined thresholds to determine if alert conditions exist.

It will be appreciated that the attitude thresholds may comprise heuristic algorithms that take a number of parameters into account, such as the recent measurement history, or interrelations between the measurements being taken. For example, since the movement of the subject is relatively slow in comparison to the rate at which measurements may be taken, a series of transitory values may be retained in a circular queue. Upon a threshold condition being, reached, the queue values may be used to corroborate the received threshold condition, whereby the condition may be verified or rejected.

It should be readily appreciated that although an acceleration sensor is capable of detecting static orientation, it will still register all manner of accelerations to which the transmitter unit is subjected. Without proper discrimination routines in firmware, spurious accelerations and electrical noise will be indistinguishable from the attitudes for which detection is being sought. For example, false triggering can occur in response to physical oscillations (such as "jiggle") and electromagnetic disturbances (such as the 60 Hz of fluorescent lighting). In order to reduce false triggering caused by the effects of these accelerations, as well as spurious electrical noise, a series of measurements may be taken at intervals, for example ¹⁄₁₂₀ second, and examined for characteristic threshold conditions. Utilizing a historical series leads to a reduced susceptibility to both mechanical and electrical disturbances, without impairing the effectiveness of detection. In addition, the use of various microcontrollers may provide for utilizing principles of digital signal processing that may include Fourier analysis, to eliminate or further reduce the probability of false alarms.

If the recorded values are found to exceed their respective attitude thresholds, they are tagged for future transmission after all other system parameters are evaluated. It will be appreciated that the communication of measurements, as represented in block 318b, allows the receiver unit to perform the extended alert processing, which may include historical data and heuristic algorithms for ascertaining the importance of the specific measurements being received.

To process a single axis of orientation, or tilt angle, from a circuit generating a PWM signal such as exemplified in FIG. 5, the orientation signal can be processed as follows. The tilt signal is polled until a first state, such as High, is detected, then a timer is started, whereupon the controller is conditioned to detect a second alternate state, such as a Low state. Upon encountering the Low sate signal, the timer is stopped and the angle associated with the time value determined, such as by threshold, calculation, or lookup table. If a specific tilt threshold is being detected, such as the aforementioned seventy degrees, the routine may check for a specific count as a threshold. In testing an implementation of attitude transmitter unit according to the acceleration sensor circuit of FIG. 6A, it was found that for tilt angles at or exceeding seventy degrees the elapsed time between a High to Low transition was less than 448 microseconds. The foregoing description is provided by way of example of a simple mechanism which may be utilized for detecting tilt angle. However, it should be appreciated that the process should include extended processing, such as the averaging of multiple readings, and the use of various heuristics and behavioral modeling which relate the various sensors to arrive at a verified tilt detection.

Referring again to FIG. 10, block 320 modifies an ALIVE signal timer, whereupon at expiration, in block 322, a flag is set to direct the transmission of an ALIVE signal later in the main loop. The ALIVE signal is preferably set to be transmitted every one to ten minutes. Use of an ALIVE signal can provide a key aspect of system reliability. If for any reason the ALIVE signal is inhibited, the associated attitude receiver unit will appropriately alert personnel so that the situation may be investigated and remediated.

A patch removal detection routine is shown by block 324, whereupon if removal has been detected a flag is set as per block 326. Measurements are shown being registered in block 328 from temperature sensors within the device; these readings are logged for qualifying data and for subsequent transmission to a remote receiver. The temperature may be read from one or more probes strategically located on the attitude transmitter unit.

It will further be appreciated that additional sensors, as mentioned previously, such as indicators of blood pressure, consciousness, and pulse rate, may be queried to gather additional information for transmission to a remote receiver unit. If transmission flags have been set within the main loop, the routine of block 330 prepares the associated data for transmission, which is subsequently transmitted as data frames as shown in blocks 332 and 334.

Data transmissions are preferably tagged with an identifier that provides transmitter identification, or a receiver address. The data is utilized for serially modulating the RF transmitter according to the specific modulation scheme required by the receiver. The embodied transmitter utilizes OOK (On/Off Keyed) encoding, wherein the RF signal is generated by turning on and off an oscillator. The main loop is then complete and execution branches back to the top of the main loop at block 312, whereupon another iteration of processing commences.

The attitude indication device of the present invention provides a mechanism for the detection and indication of positional attitude of an attitude transmitter unit that is attached to an individual. Various example embodiments for the device according to the present invention have been described. Numerous features may be included within these embodiments to facilitate the use of the system for different applications, and within differing environments. The following alternate aspects of the invention are provided by way of example.

A number of circuits may be utilized to detect the unwarranted removal of the attitude transmitter unit from a patient, or individual. Once such circuit incorporates temperature sensing within the transmitter. Referring again to FIG. 4, a pair of temperature sensors were referenced, with an outer sensor 62 configured for response to external patch temperature and an inner sensor 64 configured for response to the temperature of the individual to which the patch is attached. The inner sensor is preferably mounted directly against the skin of the wearer to minimize thermal insulation and improve the speed and accuracy of response. If the transmitter appliance remains securely in contact with the patient, the inner sensor should register a slightly higher temperature than the outer sensor. An exception would exist for high ambient temperatures that exceed body temperature, whereupon the respective temperature sense rolls would be reversed. However, it should be recognized that it would be an alert condition in itself to subject a non-ambulatory patient to such excessive ambient temperatures.

Upon device removal, the readings from the two sensors will begin to equalize, which triggers an alert signal transmission for alerting personnel to the possible removal of the attitude transmitter unit. Numerous temperature sensors exist, one being a DS1721 miniature digital thermometer™ manufactured by Dallas Semiconductor™. The DS1721U measures temperature in 0.1125 Fahrenheit degree increments, and thereby provides suitable precision. The eight-pin device is approximately 5 mm×5 mm and 1.4 mm high, and can thereby be comfortably configured into the printed circuit board. The output from the pair of DS1721 sensors is connected to the microcontroller that monitors the difference in temperature, preferably in relation to ambient temperature.

Accordingly, it will be seen that this invention allows the physical positioning, or attitude, of an individual to be detected and transmitted to a remote indication device to suit a variety of medical applications. The present invention provides specific advantages for detecting patient egress from a bed, or wheelchair, as sensed by the downward tilt of an attitude transmitter unit attached to the thigh of the individual whose position is being monitored. It should be appreciated that the described embodiments are provided by way of example and that numerous alternative, or additional, circuits and functionality may be provided without departing from the teachings of the present invention.

Although the description above contains many specificities, these should not be construed as limiting the scope of the invention but as merely providing illustrations of some of the presently preferred embodiments of this invention. Thus the scope of this invention should be determined by the appended claims and their legal equivalents. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component or method step is explicitly recited in the claims. No claim element herein is to be construed under the provisions of 35 U.S.C. 112, sixth paragraph, unless the element is expressly recited using the phrase "means for."

TABLE 1

C14, C15 Transmitter

| Item | Qty | Reference | Description |
|---|---|---|---|
| 1 | 1 | ANT1 | Antenna |
| 2 | 1 | BT1 | 3 V LIT |
| 3 | 3 | C1, C2, C3 | 0.1 uF capacitor |
| 4 | 2 | C14, C15 | 0.1 uF capacitor |
| 5 | 3 | C4, C10, C11 | 15 pF capacitor |
| 6 | 1 | C5 | 6 pF capacitor |
| 7 | 1 | C6 | 27 pF capacitor |
| 8 | 1 | C7 | 4–20 pF variable capacitor |
| 9 | 1 | C8 | 10 uF capacitor |
| 10 | 1 | C9 | 0.01 uF capacitor |
| 11 | 1 | C12 | 10 uF 16 V capacitor |
| 12 | 1 | C13 | 100 uF 10 V capacitor |
| 13 | 1 | L1 | 2.0 uH inductor |
| 14 | 1 | L2 | 12 uH inductor |
| 15 | 1 | Q1 | NE68019-ND |
| 16 | 1 | Q2 | ND5352P/SOT |
| 17 | 1 | Q3 | NDS351N/SOT |
| 18 | 1 | R1 | 1 M resistor |
| 19 | 1 | R2 | 68K resistor |
| 20 | 1 | R3 | 0 jumper/resistor |
| 21 | 1 | R4 | 10 resistor |
| 22 | 1 | R5 | 330K resistor |
| 23 | 2 | R6, R8 | 10K resistor |
| 24 | 1 | R14 | 250K resistor |
| 25 | 1 | R15 | P5E105 |
| 26 | 1 | S1 | Switch PBNO |
| 27 | 1 | U2 | PIC12C508 Microcontroller |
| 28 | 1 | U3 | MAX1675 - voltage converter and regulator |
| 29 | 1 | U4 | ADXL202E - accelerometer |
| 30 | 1 | Y1 | oscillator crystal (32 kHz) |

What is claimed is:

1. A skin patch for preventing falls, comprising:
an adhesive surface;
an accelerometer disposed within said skin patch at a preset orientation;
a marking on the skin patch for rapidly positioning the adhesive surface for fixation to skin, wherein after the fixation the accelerometer has a pre-established disposition with respect to a femur bone; and
a sensing circuit to monitor the accelerometer and to generate a signal when the accelerometer indicates a femur orientation associated with a high risk of falling;
wherein the femur orientation is selected to indicate a point in a mobility process prior to transferring a majority of upper body weight through the femur to a knee or a foot of the patient; and
wherein the selected femur orientation and the sensing circuit eliminate false positive signals with respect to allocation of personnel to respond to the high risk of falling.

2. The skin patch of claim 1 wherein said femur orientation comprises an angle from the horizontal that is between about 60° and about 80°.

3. The skin patch of claim 1 wherein said femur orientation comprises an angle from the horizontal that is about 70°.

4. The skin patch of claim 1 further including
means for detecting removal of said skin patch from said skin and
means for transmitting a patch-removal signal in response thereto.

5. The skin patch of claim 4 wherein said means for detecting removal senses a temperature change on a surface of said skin patch.

6. The skin patch of claim 1 further including
a transmitter for sending the signal from the skin patch and
a battery to activate said sensing circuit and said transmitter.

7. The skin patch of claim 1 further including
means for monitoring said battery and
means for transmitting a low-battery signal when said battery is discharged below a threshold level.

8. A system comprising:
a patch having an adhesive surface;
a marking on the patch for positioning the patch relative to a femur;
an accelerometer disposed within said patch at a preset orientation;
a sensing circuit to monitor the accelerometer and to generate a pre-fall signal when the accelerometer indicates the femur is in a pre-fall position;
a transmitter coupled to the sensing circuit to transmit said pre-fall signal as it is generated;
a battery to power said sensing circuit and said transmitter;
a receiver communicatively coupled with said transmitter, said receiver to receive said pre-fall signal and to generate an alarm in response thereto;
wherein the pre-fall position of the femur is selected to indicate a point in a mobility process prior to transferring a majority of upper body weight through the femur to a knee or a foot of the patient; and
wherein the selected pre-fall position and the sensing circuit eliminate false positive signals with respect to allocation of personnel to respond to the pre-fall signal.

9. The system of claim 8 wherein said pre-fall position is between about 60° and about 80° from horizontal.

10. The system of claim 8 wherein said pre-fall position is about 70° from horizontal.

11. The system of claim 8 further including means for detecting removal of said patch from said person and for transmitting a patch-removal signal in response thereto.

12. The system of claim 11 wherein said means for detecting removal of said patch from said person senses a temperature change on a surface of said patch.

13. The system of claim 11 wherein said receiver receives said patch-removal signal and generates an alarm in response thereto.

14. The system of claim 8 further including means for activating said sensing circuit and said transmitter.

15. The system of claim 8 further including means for monitoring said battery and for transmitting a low-battery signal when said battery is discharged below a threshold level.

16. The system of claim 15 wherein said receiver receives said low-battery signal and generates an alarm in response thereto.

* * * * *